US009260518B2

(12) United States Patent
Hilden et al.

(10) Patent No.: US 9,260,518 B2
(45) Date of Patent: Feb. 16, 2016

(54) ANTIBODIES THAT ARE CAPABLE OF SPECIFICALLY BINDING TISSUE FACTOR PATHWAY INHIBITOR

(75) Inventors: Ida Hilden, Vanloese (DK); Jes Thorn Clausen, Hoeng (DK); Lars Christian Petersen, Hoersholm (DK); Brit Binow Soerensen, Birkeroed (DK); Helle Heibroch Petersen, Koebenhavn (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/805,900

(22) PCT Filed: Jun. 30, 2011

(86) PCT No.: PCT/EP2011/060980
§ 371 (c)(1),
(2), (4) Date: Feb. 22, 2013

(87) PCT Pub. No.: WO2012/001087
PCT Pub. Date: Jan. 5, 2012

(65) Prior Publication Data
US 2013/0142804 A1    Jun. 6, 2013

Related U.S. Application Data

(60) Provisional application No. 61/362,108, filed on Jul. 7, 2010, provisional application No. 61/475,895, filed on Apr. 15, 2011.

(30) Foreign Application Priority Data

Jun. 30, 2010  (EP) .................................... 10167911
Apr. 1, 2011   (EP) .................................... 11160763

(51) Int. Cl.
*C07K 16/38*   (2006.01)
*C07K 16/28*   (2006.01)
*A61K 39/395*  (2006.01)

(52) U.S. Cl.
CPC ................ *C07K 16/28* (2013.01); *C07K 16/38* (2013.01); *A61K 39/395* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| 6,171,587 | B1  | 1/2001 | Wun et al. | |
| 8,481,030 | B2* | 7/2013 | Wang et al. | C07K 16/38 424/133.1 |
| 2010/0197896 | A1 | 8/2010 | Leung et al. | |

FOREIGN PATENT DOCUMENTS

| EP | 539975 A1 * | 5/1993 |
| EP | 867450 A1 | 9/1998 |
| JP | 6153981 A | 6/1994 |
| WO | 92/07584 | 5/1992 |
| WO | 97/09063 A1 | 3/1997 |
| WO | 2008/136848 A2 | 11/2008 |
| WO | 2010/017196 A2 | 2/2010 |
| WO | 2010/071894 A2 | 6/2010 |
| WO | 2010/072687 A1 | 7/2010 |
| WO | 2010/072691 | 7/2010 |

OTHER PUBLICATIONS

Janeway et al., Immunobiology, 3rd edition, 1997, Garland Press, pp. 3:1 to 3:11.*
William E. Paul, M.D. ed., Fundamental Immunology, 3d ed. 1993, p. 242.*
Portolano et al., J. Immunol., 1993, 150:880-887.*
Rudikoff et al., Proc Natl Acad Sci U S A. Mar. 1982;79(6):1979-83.*
Abumiya et al, Journal of Biochemistry, "An Anti-Tissue Factor Pathway Inhibitor (TFPI) Monoclonal Antibody Recognized the Third Kunitz Domain (K3) of Free-Form TFPI But Not Lipoprotein-Associated Forms in Plasma", 1995, vol. 118, No. 1, pp. 178-182.
Brodin E et al, Translational Research, "Regulation of Thrombin Generation by TFPI in Plasma Without and With Heparin", 2009, vol. 153, No. 3, pp. 124-131.
Broze et al, Journal of Thrombosis and Haemostasis, "Comparison of Cell-Surface TFPIA and B", 2005, vol. 3, pp. 2677-2683.
Carter P J, Nature Reviews, "Potent Antibody Therapeutics by Design", 2006, vol. 6, pp. 343-357.
Davies J et al, Immunotechnology, ""Affinity Improvement of Single Antibody VH Domains: Residues in a L L Three Hypervariable Regions Affect Antigen Binding"", 1996, vol. 2, No. 3, pp. 169-179.
Enjyoji K-I et al, Biochemistry, ""Effect of Heparin on the Inhibition of Factor XA by Tissue Factor Pathway Inhibitor: A Segment, GLY-PHE, of the Third Kunitz Domain Is a Heparin-Binding Site"", 1995, vol. 34, No. 10, pp. 5725-5735.
Haiwang et al, The American Journal of Pathology, ""Sepsis-Induced Coagulation in the Baboon Lung Is Associated With Decreased Tissue Factor Patway Inhibitor Coagulation in the Baboon Lung Is Associated With Decreased Tissue Factor Pathway Inhibitor"", 2007, vol. 171, No. 3, pp. 1066-1077.
Holt L J et al, Trends in Biotechnology, ""Domain Antibodies Proteins for Therapy"", 2003, vol. 21, No. 11, pp. 484-490.
Hedner U., Seminars in Hematology, "Mechanism of Action of Recombinant Activated Factor VII: an Update", 2006, vol. 43, No. 1, pp. S105-S107.
Kokawa T et al, Arteriosclerosis Thrombosis and Vascular Biology, ""Measurement of the Free Form of TFPI Antigen in Hyperlipidemia Relationship Between Free and Endothelial Cell-Associated Forms Relationship Between Free and Endothelial Cell-Associated Forms of TFPI"", 1996, vol. 16, No. 6, pp. 802-808.

(Continued)

*Primary Examiner* — Michael Szperka
(74) *Attorney, Agent, or Firm* — Jianjie Hu

(57) ABSTRACT

The invention relates to antibodies that are capable of specifically binding tissue factor pathway inhibitor (TFPI), neutralising free TFPI and reducing the clotting time of blood. Furthermore, the invention relates to polynucleotides that encode such antibodies and to cells that comprise the polynucleotides or that express the antibodies of the invention. Such antibodies have utility in the treatment of subjects with a coagulopathy, alone as well as in combination with a second agent.

16 Claims, 10 Drawing Sheets

(56) References Cited

OTHER PUBLICATIONS

Liu et al, Thrombosis and Haemostasis, ""Improved Coagulation in Bleeding Disorders by Non-Anticoagulant Sulfated Polysaccharides (NASP)"", 2006, vol. 95, No. 1, pp. 68-76.

Nakahara Y et al, Biochemistry, ""Amino Acid Sequence and Carbohydrate Structure of a Recombinant Human Tissue Factor Pathway Inhibitor Expressed in Chinese Hamster Ovary Cells: One N-and Two 0-1 Inked Carbohydrate Chains Are Located"", 1996, vol. 35, No. 20, pp. 6450-6459.

Nordfang et al, Thrombosis and Haemostasis, ""Inhibition of Extrinsic Pathway Inhibitor Shortens the Coagulation Time of Normal Plasma and of Hemophilia Plasma"", 1991, vol. 66, No. 4, pp. 464-467.

Ohkura, N. et al, Blood Coagulation and Fibrinolysis, "Monoclonal Antibody Specific for Tissue Factor Pathway Inhibitor-Factor XA Complex: Its Characterization and Application to Plasmas From Patients With Disseminated Intravascular Coagulation and . . . ", 1999, vol. 10, No. 6, pp. 309-319.

Piro et al, Journal of Thrombosis and Haemostasis, "Comparison of Cell-Surface TFPIA and B", 2005, vol. 3, pp. 2677-2683.

Smith et al, Proceedings of the National Academy of Sciences of the USA, ""Polyphosphate Modulates Blood Coagulation and Fibrinolysis"", 2006, vol. 103, No. 4, pp. 903-908.

Wark K L et al, Advanced Drug Delivery Reviews, ""Latest Technologies for the Enhancement of Antibody Affinity"", 2006, vol. 58, No. 5-6, pp. 657-670.

Winkler K et al, Journal of Immunology, ""Changing the Antigen Binding Specificity by Single Point Mutations of an ANTI-P24 (HIV-1) Antibody"", 2000, vol. 165, No. 8, pp. 4505-4514.

Zheng et al, Journal of Biological Chemistry, ""Versican G3 Domain Promotes Blood Coagulation Through Suppressing the Activity of Tissue Factor Pathway Inhibitor-1"", 2006, vol. 281, No. 12, pp. 8175-8182.

Wesselschmidt et al. "Tissue Factor Pathway Inhibitor: The Carboxy-Terminus is Required for Optimal Inhibition of Factor Xa." Blood. 1992. vol. 79(8) pp. 2004-2010.

Donahue et al. "Disposition of Tissue Factor Pathway Inhibitor During Cardiopulmonary Bypass." Journal of Thrombosis and Haemostasis, 2006, vol. 4, pp. 1011-1016.

Cunningham et al. "MMP-8 Cleaves TFPI and Decreases its Anticoagulant Activity." Blood, 2000, vol. 96, No. 11, p. 260a, Abstract#1116.

\* cited by examiner

ANTIBODIES THAT ARE CAPABLE OF SPECIFICALLY BINDING TISSUE FACTOR PATHWAY INHIBITOR

CROSS-REFERENCE TO RELATED APPLICATIONS

This application is a 35 U.S.C. §371 National Stage application of International Application PCT/EP2011/060980, filed Jun. 30, 2011 (WO 2012/001087 A1), which claimed priority of European Patent Application 10167911.6, filed Jun. 30, 2010 and European Patent Application 11160763.6, filed Apr. 1, 2011; this application claims priority under 35 U.S.C. §119 of U.S. Provisional Application 61/362108, filed Jul. 7, 2010 and U.S. Provisional Application 61/475895, filed Apr. 15, 2011.

FIELD OF THE INVENTION

The present invention relates to antibodies that are capable of specifically binding the C-terminal of tissue factor pathway inhibitor (TFPI) and which are thus capable of neutralising the free pool of TFPI. The invention also relates to uses for such antibodies, such as therapeutic and pharmaceutical uses.

In accordance with 37 C.F.R. §1.52(e)(5), Applicants enclose herewith the Sequence Listing for the above-captioned application entitled "SEQUENCE LISTING", created on Nov. 28, 2012. The Sequence Listing is made up of 55,340 bytes, and the information contained in the attached "SEQUENCE LISTING" is identical to the information in the specification as originally filed. No new matter is added.

BACKGROUND OF THE INVENTION

In subjects with a coagulopathy, such as in human beings with haemophilia A and B, various steps of the coagulation cascade are rendered dysfunctional due to, for example, the absence or insufficient presence of a coagulation factor. Such dysfunction of one part of the coagulation cascade results in insufficient blood coagulation and potentially life-threatening bleeding, or damage to internal organs, such as the joints. Subjects such as human beings with haemophilia A and B may receive coagulation factor replacement therapy such as exogenous Factor VIII or Factor IX, respectively. However, such patients are at risk of developing "inhibitors" (antibodies) to such exogenous factors, rendering formerly efficient therapy ineffective. Furthermore, exogenous coagulation factors may only be administered intravenously, which is of considerable inconvenience and discomfort to patients. For example, infants and toddlers may have to have intravenous catheters surgically inserted into a chest vein, in order for venous access to be guaranteed. This leaves them at great risk of developing bacterial infections and thrombotic complications. Subjects with a coagulopathy may only receive therapy after a bleed has commenced, rather than as a precautionary measure, which often impinges upon their general quality of life. Thus, there are still many unmet medical needs in the haemophilia community, in particular, and in subjects with coagulopathies, in general.

The coagulation cascade is normally set into motion upon vessel wall injury, which exposes sub-endothelial tissue factor (TF) to the components of circulating blood. In brief, TF forms a complex with Factor VII/Factor VIIa (FVII/FVIIa) on the surface of TF-expressing cells. This complex activates Factor X (FX) to Factor Xa (FXa) which, with Factor Va (FVa) as cofactor, leads to the generation of a limited amount of thrombin (FIIa). Small amounts of thrombin activate platelets, which results in surface exposure of phospholipids that support the binding of the tenase complex, Factor VIIIa/Factor IXa (FVIIIa/FIXa). The tenase complex activates large amounts of FX to FXa, which subsequently results in the generation of a large amount of thrombin. A full thrombin burst is needed for the formation of a mechanically strong fibrin structure and stabilization of the haemostatic plug.

In individuals with haemophilia, FVIII or FIX is present at low levels, or may be entirely absent. Due to the lack of tenase activity, the capacity to generate FXa is low and insufficient to support the propagation phase of coagulation. In contrast, the TF-mediated initiation phase of coagulation is not dependent on the formation of the tenase complex. Initiation of coagulation via the TF-pathway will, however, be blocked by plasma inhibitors shortly after the initial FXa generation. One such inhibitor is tissue factor pathway inhibitor (TFPI), which inhibits both FXa and TF/FVIIa and plays a key role as a feed-back inhibitor of on-going coagulation. TFPI is a strong inhibitor of the TF-FVIIa complex only in the presence of FXa. Thus, efficient inhibition of TF/FVIIa requires generation of FXa, formation of the FXa/TFPI complex, and a subsequent formation of the ternary TF/FVIIa/FXa/TFPI complex.

Several pools of TFPI exist in vivo. A major fraction is bound to the vascular endothelium, a minor fraction is associated with lipoproteins in the blood, a small fraction is present in platelets and, finally, a small amount exists as free, circulating TFPI. Furthermore, TFPI exists as TFPIalpha, TFPIbeta and TFPIgamma forms. Neutralization of the inhibitory activity of certain fractions of TFPI may prove efficient in treatment of undesired bleedings.

Antibodies that are capable of binding TFPI are known in the art. Several documents disclose antibodies that are capable of binding to the K3 domain of TFPI, namely:

J. Biochem, 1995, 118 (1): 178-182.
Blood Coagul. Fibrinolyis, 1999, 10 (6): 309-19.
JP6153981A.

These references do not disclose TFPI antibodies for the treatment of subjects with a coagulopathy.

There is still a need in the art of medicine for pharmaceuticals which may be used to enhance coagulation. There is a need for pharmaceuticals which may be administered not only intravenously but also by other routes of administration, such as subcutaneously. Thus, there is a need for pharmaceuticals, such as antibodies, which are pro-coagulant even when administered in low doses and/or which have a high bioavailability. Furthermore, there is a need for pharmaceuticals, such as antibodies, which are suitable for the prophylactic treatment of individuals with a congenital or acquired coagulopathy such as haemophilia A, haemophilia B, haemophilia A with inhibitors or haemophilia B with inhibitors. More specifically, there is a need for pharmaceuticals, such as antibodies, that lower the threshold for FVIII or FIX activity in individuals with haemophilia A and haemophilia B, respectively. Within the particular realm of antibodies that are capable of binding TFPI, there is a need for antibodies which do not bind to all pools of TFPI, such as antibodies which do not affect the function of endothelial cell-bound TFPI, such as the GPI-anchored pool of TFPI. More specifically, there is a need for TFPI antibodies that demonstrate dose linearity with respect to their half-life in plasma.

Disclosed herein are antibodies which are suitable for use as pharmaceuticals. Such antibodies may have a substantial impact upon the quality of life of—not least—individuals with haemophilia A or B, with or without inhibitors.

SUMMARY OF THE INVENTION

The inventors have developed monoclonal antibodies that are capable of specifically binding to the C-terminal of full length tissue factor pathway inhibitor (TFPI), wherein "C-terminal" is herein defined as that portion of TFPI which is, or which corresponds to, amino acid residues 186-276 of full length human TFPI (SEQ ID NO:1). The present invention relates to these antibodies and to other antibodies that are derived from these antibodies and/or that have similar binding properties and that are capable of modulating the activity of free TFPI.

Antibodies of the invention may be capable of specifically binding residues selected from the group consisting of P186, S187, L190, P192, A193, D194, R195, G196, L197, C198, R199, A200, N201, E202, N203, R204, F205, Y206, Y207, N208, K213, R215, P216, F217, K218, Y219, S220, N225, E226, N227, N228, T230, S231, K232, Q233, E234, L236, R237, K240, K241, G242, F243, I244, Q245, R246, I247, S248, K249, G250, G251, L252, I253, K254, T255, K256, R257, K258, R259, K260, K261, Q262, R263, V264, K265, I266, A267, Y268, E269, E270, I271, F272, V273, K274, N275 and M276 of SEQ ID NO: 1.

Antibodies of the invention may be capable of specifically binding residues selected from the group consisting of P186, S187, L190, P192, A193, D194, R195, G196, L197, C198, R199, A200, N201, E202, N203, R204, F205, Y206, Y207, N208, K213, R215, P216, F217, K218, Y219, S220, N225, E226, N227, N228, T230, S231, K232, Q233, E234, L236 and R237 of SEQ ID NO: 1.

Antibodies of the invention may be capable of specifically binding residues selected from the group consisting of K240, K241, G242, F243, I244, Q245, R246, I247, S248, K249, G250, G251, L252, I253, K254, T255, K256, R257, K258, R259, K260, K261, Q262, R263, V264, K265, I266, A267, Y268, E269, E270, I271, F272, V273, K274, N275 and M276 of SEQ ID NO: 1.

One particular antibody comprises the heavy chain variable region of SEQ ID NO: 7 and the light chain variable region of SEQ ID NO: 5. Another particular antibody comprises the heavy chain variable region of SEQ ID NO: 9 and the light chain variable region of SEQ ID NO: 11. A third particular antibody comprises the heavy chain variable region of SEQ ID NO: 13 and the light chain variable region of SEQ ID NO: 15.

The invention also provides polynucleotides which encode an antibody of the invention, such as polynucleotides which encode an antibody light chain and/or an antibody heavy chain of the invention.

The invention also provides pharmaceutical compositions comprising an antibody or polynucleotide of the invention and a pharmaceutically acceptable carrier or diluent.

The antibodies, polynucleotides and compositions of the invention are also provided for use in the treatment or prevention of a coagulopathy or the stimulation of blood clotting. That is, the invention provides a method for the treatment or prevention of a coagulopathy, or the stimulation of blood clotting, said method comprising administering to a patient in need thereof a therapeutically or prophylactically effective amount of an antibody, polynucleotide or composition of the invention.

BRIEF DESCRIPTION OF THE SEQUENCE LISTING

SEQ ID NO: 1 provides the amino acid sequence of full length human TFPI (signal peptide sequence omitted).

SEQ ID NO: 2 provides the amino acid sequence of truncated TFPI (1-239).

SEQ ID NO: 3 provides the amino acid sequence of truncated TFPI (1-245).

SEQ ID NO: 4 provides the nucleic acid sequence (signal peptide sequence omitted) of the variable heavy (VH) domain of anti-TFPI4F110 (also designated mAb 4F110).

SEQ ID NO: 5 provides the amino acid sequence (signal peptide sequence omitted) of the variable heavy (VH) domain of anti-TFPI4F110.

SEQ ID NO: 6 provides the nucleic acid sequence (signal peptide sequence omitted) of the variable light (VL) domain of anti-TFPI4F110.

SEQ ID NO: 7 provides the amino acid sequence (signal peptide sequence omitted) of the variable light (VL) domain of anti-TFPI4F110.

SEQ ID NO: 8 provides the nucleic acid sequence (signal peptide sequence omitted) of the variable heavy (VH) domain of anti-TFPI22F66.

SEQ ID NO: 9 provides the amino acid sequence (signal peptide sequence omitted) of the variable heavy (VH) domain of anti-TFPI22F66.

SEQ ID NO: 10 provides the nucleic acid sequence (signal peptide sequence omitted) of the variable light (VL) domain of anti-TFPI22F66.

SEQ ID NO: 11 provides the amino acid sequence (signal peptide sequence omitted) of the variable light (VL) domain of anti-TFPI22F66.

SEQ ID NO: 12 provides the nucleic acid sequence (signal peptide sequence omitted) of the variable heavy (VH) domain of anti-TFPI22F71.

SEQ ID NO: 13 provides the amino acid sequence (signal peptide sequence omitted) of the variable heavy (VH) domain of anti-TFPI22F71.

SEQ ID NO: 14 provides the nucleic acid sequence (signal peptide sequence omitted) of the variable light (VL) domain of anti-TFPI22F71.

SEQ ID NO: 15 provides the amino acid sequence (signal peptide sequence omitted) of the variable light (VL) domain of anti-TFPI22F71.

SEQ ID NO: 16 provides the nucleic acid sequence of the reverse primer that was used for HC (VH domain) amplification.

SEQ ID NO: 17 provides the nucleic acid sequence of the reverse primer that was used for TFPI22F66 and TFPI22F71 LC (VL domain) amplification.

SEQ ID NO: 18 provides the nucleic acid sequence of the reverse primer that was used for TFPI4F110 LC amplification.

SEQ ID NO: 19 provides the amino acid sequence of Factor VII/Factor VIIa.

SEQ ID NO: 20 provides the amino acid sequence of Factor VIII.

SEQ ID NO: 21 provides the amino acid sequence of Factor IX.

SEQ ID NO: 22 provides the amino acid sequence of truncated TFPI (1-240).

SEQ ID NO: 23 provides the amino acid sequence of truncated TFPI (1-241).

SEQ ID NO: 24 provides the amino acid sequence of truncated TFPI (1-242).

SEQ ID NO: 25 provides the amino acid sequence of truncated TFPI (1-243).

SEQ ID NO: 26 provides the amino acid sequence of truncated TFPI (1-244).

DESCRIPTION OF THE INVENTION

Figure 1:
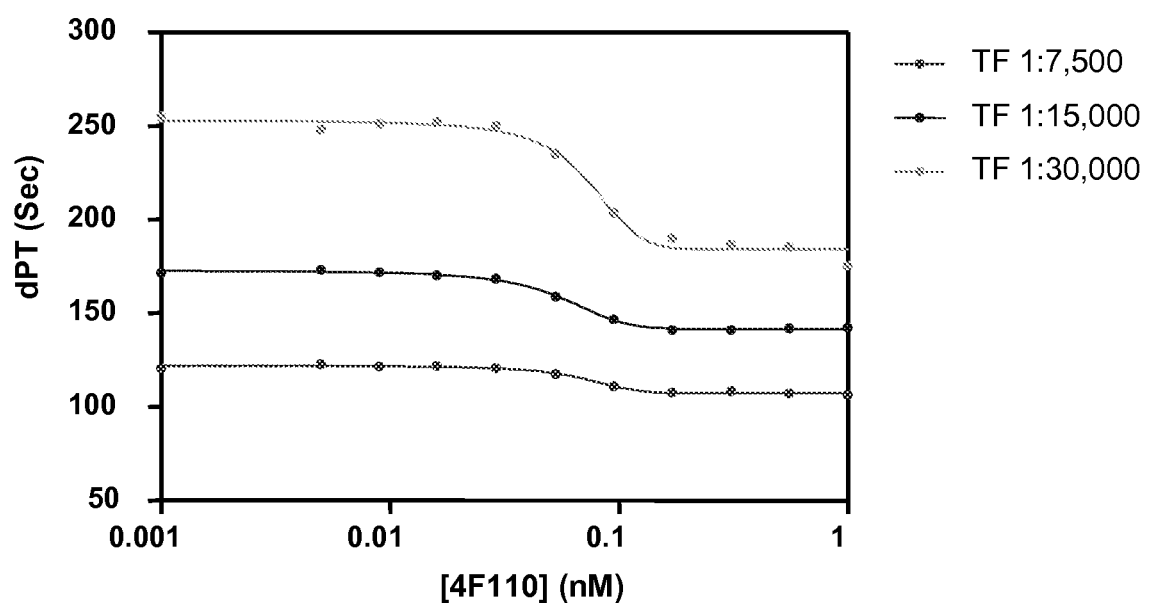
FIG. 1 shows the effect of the 4F110 TFPI antibody on TF-induced clot formation. Clotting time was measured with a dilute PT assay at various fixed concentrations of TF (Innovin® diluted 1:7,500; 1:15,000; 1:30,000) and antibody (0.005-1 nM).

The invention relates to antibodies that are capable of specifically binding full-length tissue factor pathway inhibitor (TFPI), such as antibodies that bind to the "C-terminal" of TFPI. Such antibodies may specifically bind the C-terminal domain and/or the Kunitz 3 (K3) domain of TFPI; that is, they may bind to the "C-terminal" but may not bind to the Kunitz 1 (K1) domain of TFPI, the Kunitz 2 (K2) domain of TFPI, or to other similar molecules. Antibodies of the invention may not bind to a TFPI molecule that comprise the K1 and/or K2 domain but that lack that portion of TFPI which is C-terminal to the K2 domain. Antibodies of the invention may be incapable of binding truncated TFPI, such as C-terminal truncated TFPI. Truncated forms of TFPI that may not be bound by the antibodies of the invention include the polypeptide of SEQ ID NO: 2 and a polypeptide having the sequence of amino acids 1 to 161 of SEQ ID NO: 1. Alternatively, the antibodies may bind the K1 domain of TFPI, the K2 domain of TFPI, or other molecules such as truncated TFPI molecules with a low affinity compared to that with which they bind the C-terminal of TFPI.

The term "TFPI", as used herein, encompasses any naturally occurring form of TFPI which may be derived from any suitable organism. For example, TFPI for use as described herein may be vertebrate TFPI, such as mammalian TFPI, such as TFPI from a primate (such as a human); a rodent (such as a mouse or a rat), a lagomorph (such as a rabbit), or an artiodactyl (such a cow, sheep, pig or camel). Preferably, the TFPI is human TFPI. The TFPI may be a mature form of TFPI such as a TFPI protein that has undergone post-translational processing within a suitable cell. Such a mature TFPI protein may, for example, be glycosylated. The TFPI may be a full length TFPI protein. The term TFPI also encompasses variants, isoforms and other homologs of such TFPI molecules. Variant TFPI molecules may have the same type of activity as naturally occurring TFPI, such as the ability to neutralize the catalytic activity of FXa, or the ability to inhibit a complex of TF-FVIIa/FXa.

The term "C-terminal", as used herein, refers to any part of TFPI that is C-terminal to the amino acid residue which corresponds to amino acid 187 of human TFPI (SEQ ID NO: 1). The term "C-terminal" specifically excludes the Kunitz 1 (K1) and Kunitz 2 (K2) domains of TFPI. On the other hand, the term "C-terminal" includes parts of TFPI that are within the Kunitz 3 (K3) domain of TFPI (amino acids 188-238) and/or parts of TFPI that include amino acids 240-276.

"Free TFPI" is the in vivo pool of TFPI that contains an available "C-terminal". The term "free TFPI" refers to the soluble pool of TFPI in plasma. Other pools of TFPI, that are not "free TFPI", are GPI-anchored TFPI and lipoprotein bound TFPI. In contrast to free TFPI, these pools of TFPI do not have a C-terminal that is available for binding to, eg., an antibody. Antibodies of the invention may be capable of specifically binding free TFPI, but may not be capable of specifically binding GPI-anchored TFPI. Antibodies of the invention may be capable of specifically binding free TFPI, but may not be capable of specifically binding lipoprotein bound TFPI.

Thus, the invention relates to antibodies that may be capable of modulating the activity of free TFPI, only. Such antibodies may possess the ability to shorten clotting time. For example, an antibody of the invention may have the ability to shorten clotting time in human FVIII-deficient plasma or human FIX-deficient plasma, or to reduce time to clot as measured in a thromboelastography (TEG) analysis of human whole blood.

Antibodies of the invention may be monoclonal antibodies in the sense that they are made by identical immune cells that are all clones of the same parent cell. Antibodies of the invention may be produced, screened and purified using the methods described in the Examples. Antibodies of the invention may also be produced by means of other methods known to the person skilled in the art, such as a phage display or a yeast display. Once produced, antibodies may be screened for binding to, for example, full length TFPI, truncated TFPI (1-161), truncated TFPI (1-239), truncated TFPI (1-240), truncated TFPI (1-241), truncated TFPI (1-242), truncated TFPI (1-243), truncated TFPI (1-244), truncated TFPI (1-245) and truncated TFPI (1-246) using the methods described in the Examples.

The term "antibody" herein refers to a protein, derived from a germline immunoglobulin sequence, that is capable of specifically binding to an antigen or a portion thereof. The term includes full length antibodies of any isotype (that is, IgA, IgE, IgG, IgM and/or IgY) and any single chain thereof.

The term "antibody", as referred to herein, includes whole antibodies and any antigen binding fragment (i.e., "antigen-binding portion") or single chains thereof. An antibody refers to a glycoprotein comprising at least two heavy chains (HC) and two light chains (LC) that are inter-connected by disulfide bonds; or an antigen binding portion thereof. Each heavy chain is comprised of a heavy chain variable region (VH) and a heavy chain constant region (CH). Each light chain is comprised of a light chain variable region (VL) and a light chain constant region (CL). The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

Examples of antigen-binding fragments of the invention include Fab, Fab', F(ab)2, F(ab')2, F(ab)S, Fv (typically the VL and VH domains of a single arm of an antibody), single-chain Fv (scFv; see e.g.. Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al., Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S:1126-1136; WO2005040219, and published U.S. Patent Applications 20050238646 and 20020161201.

"Fab fragments", including "Fab" and "Fab(ab')$_2$" fragments, of an antibody are derived from said antibody by cleavage of the heavy chain in the hinge region on the N-terminal or C-terminal side the hinge cysteine residues connecting the heavy chains of the antibody. A "Fab" fragment includes the variable and constant domains of the light chain and the variable domain and the first constant domain (CH1) of the heavy chain. "F(ab')$_2$" fragments comprise a pair of "Fab" fragments that are generally covalently linked by their hinge cysteines. A Fab' is formally derived from a F(ab')$_2$ fragment by cleavage of the hinge disulfide bonds connecting the heavy chains in the F(ab')$_2$. Other chemical couplings than disulfide linkages of antibody fragments are also known in the art. A Fab fragment retains the ability of the parent antibody to bind to its antigen, potentially with a lower affinity. F(ab')$_2$ fragments are capable of divalent binding, whereas Fab and Fab' fragments can bind monovalently. Generally, Fab fragments lack the constant CH2 and CH3 domains, i.e. the Fc part, where interaction with the Fc receptors would occur. Thus, Fab fragments are in general devoid of effector functions. Fab fragments may be produced by methods known in the art, either by enzymatic cleavage of an antibody, e.g. using papain to obtain the Fab or pepsin to obtain the F(ab')$_2$, or Fab fragmants may be produced recombinantly using techniques that are well known to the person skilled in the art.

An "Fv" fragment is an antibody fragment that contains a complete antigen recognition and binding site, and generally comprises a dimer of one heavy and one light chain variable domain in association that can be covalent in nature, for example in a single chain variable domain fragment (scFv). It is in this configuration that the three hypervariable regions of each variable domain interact to define an antigen-binding site on the surface of the VH-VL dimer. Collectively, the six hypervariable regions or a subset thereof confer antigen binding specificity to the antibody. However, even a single variable domain comprising only three hypervariable regions specific for an antigen has the ability to recognize and bind antigen, although usually at a lower affinity than the entire binding site (Cai & Garen, Proc. Natl. Acad. Sci. USA, 93: 6280-6285, 1996). For example, naturally occurring camelid antibodies that only have a heavy chain variable domain (VHH) can bind antigen (Desmyter et al., J. Biol. Chem., 277: 23645-23650, 2002; Bond et al., J. Mol. Biol. 2003; 332: 643-655).

"Single-chain Fv" or "scFv" antibody fragments comprise the VH and VL domains of antibody, where these domains are present in a single polypeptide chain. Generally, the Fv polypeptide further comprises a polypeptide linker between the VH and VL domains that enables the scFv to form the desired structure for antigen binding. For a review of scFv, see Pluckthun, 1994, In: The Pharmacology of Monoclonal Antibodies, Vol. 113, Rosenburg and Moore eds. Springer-Verlag, New York, pp. 269-315.

The term "diabodies" refers to small antibody fragments with two antigen-binding sites, in which fragments comprise a heavy chain variable domain (VH) connected to a light chain variable domain (VL) in the same polypeptide chain (VH and VL). By using a linker that is too short to allow pairing between the two variable domains on the same chain, the variable domains are forced to pair with complementary domains of another chain, creating two antigen-binding sites. Diabodies are described more fully, for example, in EP 404, 097; WO 93/11161; and Hollinger et al., 1993, Proc. Natl. Acad. Sci. USA, 90:6444-6448.

The expression "linear antibodies" refers to antibodies as described in Zapata et al., 1995, Protein Eng., 8(10):1057-1062. Briefly, these antibodies contain a pair of tandem Fd segments (VH-CH1-VH-CH1) that, together with complementary light chain polypeptides, form a pair of antigen binding regions. Linear antibodies can be bispecific or monospecific.

The term "monobody" as used herein, refers to an antigen binding molecule with a heavy chain variable domain and no light chain variable domain. A monobody can bind to an antigen in the absence of light chains and typically has three hypervariable regions, for example CDRs designated CDRH1, CDRH2, and CDRH3. A heavy chain IgG monobody has two heavy chain antigen binding molecules connected by a disulfide bond. The heavy chain variable domain comprises one or more hypervariable regions, preferably a CDRH3 or HVL-H3 region.

Antibody fragments may be obtained using conventional recombinant or protein engineering techniques, and the fragments may be screened for binding to full length TFPI, truncated TFPI (1-161), truncated TFPI (1-239), truncated TFPI (1-240), truncated TFPI (1-241), truncated TFPI (1-242), truncated TFPI (1-243), truncated TFPI (1-244), truncated TFPI (1-245) and truncated TFPI (1-246) in the same manner as intact antibodies.

Antibody fragments of the invention may be made by truncation, e.g. by removal of one or more amino acids from the N and/or C-terminal ends of a polypeptide. Fragments may also be generated by one or more internal deletions.

An antibody of the invention may be, or may comprise, a fragment of the MuTFPI4F110 antibody, the MuTFPI22F66 antibody, the MuTFPI22F71 antibody, the MuTFPI 22F74 antibody, the MuTFPI 22F79 antibody, the MuTFPI 22F132 antibody, or a variant of any one of these antibodies. An antibody of the invention may be, or may comprise, an antigen binding portion of one of these antibodies, or variants thereof. For example, the antibody of the invention may be a Fab fragment of one of these antibodies or variants thereof, or it may be a single chain antibody derived from one of these antibodies, or a variant thereof.

The MuTFPI4F110 antibody has a variable heavy chain sequence as shown in SEQ ID NO: 5 and a variable light chain sequence as shown in SEQ ID NO: 7. An antibody of the invention may comprise this variable heavy chain sequence and/or this variable light chain sequence. The MuTFPI4F110 antibody has the CDR sequences shown at amino acid residues 31 to 35, 50 to 66 and 99 to 107 of SEQ ID NO: 5 and amino acid residues 24 to 34, 50 to 56 and 89 to 97 of SEQ ID NO: 7. An antibody of the invention may comprise 1, 2, 3, 4, 5 or all 6 of these CDR sequences. An antibody of the invention may comprise amino acid residues 99 to 107 of SEQ ID NO: 5.

The MuTFPI22F66 antibody has a variable heavy chain sequence as shown in SEQ ID NO: 9 and a variable light chain sequence as shown in SEQ ID NO: 11. An antibody of the invention may comprise this variable heavy chain sequence and/or this variable light chain sequence. The MuTFPI22F66 antibody has the CDR sequences shown at amino acid residues 31 to 35, 50 to 66 and 99 to 106 of SEQ ID NO: 9 and amino acid residues 24 to 33, 49 to 55 and 88 to 96 of SEQ ID NO: 11. An antibody of the invention may comprise 1, 2, 3, 4, 5 or all 6 of these CDR sequences. An antibody of the invention may comprise amino acid residues 99 to 106 of SEQ ID NO: 9.

The MuTFPI22F71 antibody has a variable heavy chain sequence as shown in SEQ ID NO: 13 and a variable light chain sequence as shown in SEQ ID NO: 15. An antibody of the invention may comprise this variable heavy chain sequence and/or this variable light chain sequence. The MuTFPI22F71 antibody has the CDR sequences shown at amino acid residues 31 to 35, 50 to 66 and 99 to 111 of SEQ ID NO: 13 and amino acid residues 24 to 38, 54 to 60 and 93 to 101 of SEQ ID NO: 15. An antibody of the invention may comprise 1, 2, 3, 4, 5 or all 6 of these CDR sequences. An antibody of the invention may comprise amino acid residues 99 to 111 of SEQ ID NO: 13.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, rat or rabbit, having a genome comprising a human heavy chain transgene and a light chain transgene fused to an immortalized cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanised antibody" is intended to refer to a human/non-human chimeric antibody that contains a minimal sequence (CDR regions) derived from non-human immunoglobulin. Humanized antibodies are thus human immunoglobulins (recipient antibody) in which residues from a hyper-variable region of the recipient are replaced by residues from a hypervariable region of a non-human species (donor antibody) such as from a mouse, rat, rabbit, or non-human primate, having the desired specificity, affinity, and capacity. In some instances, FR residues of the human immunoglobulin are replaced by corresponding non-human residues. An example of such a modification is the introduction of one or more so-called back-mutations.

The term "humanized antibody derivative" refers to any modified form of the humanized antibody, such as a conjugate of the antibody and another agent or antibody.

Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin.

The "fragment crystallizable" region ("Fc region"/"Fc domain") of an antibody is the N-terminal region of an antibody, which comprises the constant CH2 and CH3 domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. Preferably, a modified Fc domain comprises one or more, and perhaps all of the following mutations that will result in decreased affinity to certain Fc receptors (L234A, L235E, and G237A) and in reduced C1q-mediated complement fixation (A330S and P331S), respectively (residue numbering according to the EU index).

In one aspect, antibodies of the invention may be engineered to include modifications within the Fc region, typically to alter one or more functional properties of the antibody, such as serum half-life, complement fixation, Fc receptor binding, protein stability and/or antigen-dependent cellular cytotoxicity, or lack thereof. Furthermore, an antibody of the invention may be chemically modified (e.g., one or more chemical moieties can be attached to the antibody) or be modified to alter its glycosylation, again to alter one or more functional properties of the antibody.

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CHI is modified such that the number of cysteine residues in the hinge region is altered, e.g., increased or decreased. This approach is described further for instance in U.S. Pat. No. 5,677,425 by Bodmer et al.

The constant region may further be modified to stabilize the antibody, e.g., to reduce the risk of a bivalent antibody separating into two monovalent VH-VL fragments. For example, in an IgG4 constant region, residue S241 may be mutated to a proline (P) residue to allow complete disulphide bridge formation at the hinge (see, e.g., Angal et al., Mol Immunol. 199S; 30:105-8).

An antibody of the invention will have the ability to bind to TFPI. An antibody of the invention is, preferably, capable of specifically binding the C-terminal of TFPI. That is, it is capable of binding the C-terminal of TFPI with a greater binding affinity than that with which it binds to the K1 domain of TFPI, the K2 domain of TFPI, or another molecule.

The target molecule of an antibody of the invention may be any TFPI molecule as described herein, such as a naturally occurring TFPI molecule, a fully mature TFPI molecule or a full-length TFPI molecule. The TFPI molecule may be in a form that is present in vivo. The target molecule may be TFPI in a form that is present in plasma in vivo. The antibody of the invention may be able to discriminate between the various naturally occurring forms of TFPI, binding to some but not to others. For example, antibodies of the invention may not be capable of binding naturally occurring, truncated forms of TFPI that do not comprise a K3 domain and/or a carboxy terminal domain. However, the target molecule may be a truncated TFPI molecule that comprises a K3 domain and/or a carboxy terminal. The target molecule may be a variant or a fragment of a TFPI molecule. The target molecule may consist of, or may comprise, the amino acid sequence of SEQ ID NO: 1, or a fragment or other variant thereof. Target molecules comprise a suitable epitope for antibody binding, such as the epitope described herein.

The target molecule may comprise five or more, ten or more, fifteen or more, twenty or more, twenty five or more, or thirty or more surface accessible residues of TFPI or of a particular region of TFPI, such as the K3 domain or the C-terminal of TFPI. A surface accessible residue is a residue having more than 40% relative accessibility.

Methods of measuring surface accessibility are well known in the art, having first been described by Lee & Richards in 1971 [B. Lee and F. M. Richards, "The Interpretation of Protein Structures: Estimation of Static Accessibility" J. Mol. Biol. 55, 379-400 (1971)]. Surface accessibilities may be calculated using the computer program Quanta 2005, from Accelrys Inc., using the atomic coordinates originating from, for example, X-ray structures or homology built structures.

The term "binding affinity" is herein used as a measure of the strength of a non-covalent interaction between two molecules, e.g. an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation, or binding, constant ($K_D$). In turn, $K_D$ can be determined by measurement of the kinetics of complex formation and dissociation, e.g. by the SPR method (Biacore). The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D = k_d/k_a$.

Following the above definition, binding affinities associated with different molecular interactions, e.g. comparison of the binding affinity of different antibodies for a given antigen, may be compared by comparison of the $K_D$ values for the individual antibody/antigen complexes.

Similarly, the specificity of an interaction may be assessed by determination and comparison of the $K_D$ value for the interaction of interest, e.g. a specific interaction between an antibody and an antigen, with the $K_D$ value of an interaction not of interest.

Typically, the $K_D$ for the antibody with respect to the target will be 2-fold, preferably 5-fold, more preferably 10-fold less than $K_D$ with respect to the other, non-target molecule such as unrelated material or accompanying material in the environment. More preferably, the $K_D$ will be 50-fold less, such as 100-fold less, or 200-fold less; even more preferably 500-fold less, such as 1,000-fold less, or 10,000-fold less.

The value of this binding constant can be determined directly by well-known methods, and can be computed even for complex mixtures by methods such as those, for example, set forth in Caceci et al. (Byte 9:340-362, 1984). For example, the $K_D$ may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art, including for example, ELISAs, Western blots, RIAs, and flow cytometry analysis. The binding kinetics and binding affinity of the antibody also can be assessed by standard assays known in the art, such as Surface Plasmon Resonance (SPR), e.g. by using a Biacore™ system.

A competitive binding assay can be conducted in which the binding of the antibody to the target is compared to the binding of the target by another ligand of that target, such as another antibody. The concentration at which 50% inhibition occurs is known as the Ki. Under ideal conditions, the Ki is equivalent to $K_D$. The Ki value will never be less than the $K_D$, so measurement of Ki can conveniently be substituted to provide an upper limit for $K_D$.

An antibody of the invention may have a $K_D$ for its target of $1 \times 10^{-7}$M or less, $1 \times 10^{-8}$M or less, or $1 \times 10^{-9}$M or less, or $1 \times 10^{-10}$ M or less, $1 \times 10^{-11}$ M or less, or $1 \times 10^{-12}$ M or less. The $K_D$ of an antibody of the current invention may be less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.025 nM, such as less than 0.015 nM, such as less than 0.10 nM.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. An antibody of the invention is preferably capable of binding to its target with an affinity that is at least two-fold, 10-fold, 50-fold, 100-fold 200-fold, 500-fold, 1,000-fold or 10,000-fold or greater than its affinity for binding to another non-target molecule.

The antibody of the current invention may be capable of neutralising TFPI inhibition of the FVIIa/TF/FX complex.

The antibody of the current invention may be capable of binding TFPI such that the percentage of free TFPI in a subject is reduced to less than 50%, such as less than 30%, such as less than 29%, such as less than 28%, such as less than 27%, such as less than 26%, such as less than 25%, such as less than 24%, such as less than 23%, such as less than 22%, such as less than 21%, such as less than 20%, such as less than 19%, such as less than 18%, such as less than 17%, such as less than 16%, such as less than 15%, such as less than 14%, such as less than 13%, such as less than 12%, such as less than 11%, such as less than 10%, such as less than 9%, such as less than 8%, such as less than 7%, such as less than 6%, such as less than 5%, such as less than 4%, such as less than 3%, such as less than 2%, such as less than 1%, such as between 1% and 0%.

The term "complementarity-determining region" ("CDR") or "hypervariable region", when used herein, refers to the amino acid residues of an antibody that are responsible for antigen binding. The CDRs are generally comprised of amino acid residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

An antibody of the invention may comprise a CDR region from one or more of the specific antibodies disclosed herein, such as a CDR region from within SEQ ID NOs: 5, 7, 9, 11, 13 or 15. The CDR sequences within the light chain of an antibody of the invention may be identified at: amino acids 24 to 34, 50 to 56 and 89 to 97 of SEQ ID NO: 7; amino acids 24 to 33, 49 to 55 and 88 to 96 of SEQ ID NO: 11; amino acids 24 to 38, 54 to 60 and 93 to 101 of SEQ ID NOs: 15. The CDR sequences within the heavy chain of an antibody of the invention may be identified at: amino acids 31 to 35, 50 to 66 and 99 to 107 of SEQ ID NO: 5; at amino acids 31 to 35, 50 to 66 and 99-106 of SEQ ID NO: 9; amino acids 31 to 35, 50 to 66 and 99-106 of SEQ ID NO: 9; at amino acids 31 to 35, 50 to 66 and 99-111 of SEQ ID NO: 13.

An antibody of the invention may comprise any one or more of these CDR sequences. An antibody of the invention may comprise the CDR3 heavy chain sequence of one of the antibodies described herein, e.g. amino acids 99 to 107 of SEQ ID NO: 5, 99 to 106 of SEQ ID NO: 9 or 99 to 111 of SEQ ID NO: 13. An antibody of the invention may comprise all six CDRs from one of the specific antibodies described herein such as the CDR amino acids indicated above from SEQ ID NO: 5 and SEQ ID NO: 7, the CDR amino acids indicated above from SEQ ID NO: 9 and SEQ ID NO: 11 or the CDR amino acids indicated above from SEQ ID NO: 13 and SEQ ID NO: 15.

The term "epitope", as used herein, is defined in the context of a molecular interaction between an "antigen binding polypeptide" (Ab) and its corresponding "antigen" (Ag). The term antigen (Ag) refers to the molecular entity used for immunization of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunization process for raising the Ab. Thus, for Abs that bind to the C-terminal of TFPI, both full-length TFPI, truncated TFPI and other variants of TFPI that comprise the C-terminal portion of TFPI are referred to as an Ag.

Generally, the term "epitope" refers to the area or region on an Ag to which an Ab specifically binds, i.e. the area or region in physical contact with the Ab. A protein epitope may comprise amino acid residues in the Ag that are directly involved in binding to a Ab (also called the immunodominant component of the epitope) and other amino acid residues, which are not directly involved in the binding, such as amino acid residues of the Ag which are effectively blocked by the Ab (in other words, the amino acid residue is within the "solvent-excluded surface" and/or the "footprint" of the Ab). The term epitope herein includes both types of binding sites in any particular region of the K3 domain or the C-terminal domain of TFPI that specifically binds to an anti-TFPI antibody, or another "C-terminal"-specific agent according to the invention, unless otherwise stated (e.g., in some contexts the invention relates to antibodies that bind directly to particular amino acid residues). The "C-terminal" may comprise a number of different epitopes, which may include, without limitation, (1) linear peptide antigenic determinants, (2) conformational antigenic determinants which consist of one or more non-contiguous amino acids located near each other in the mature C-terminal conformation; and (3) post-translational antigenic determinants which consist, either in whole or part, of molecular structures covalently attached to the "C-terminal", such as carbohydrate groups.

The epitope for a given antibody (Ab)/antigen (Ag) pair can be defined and characterized at different levels of detail using a variety of experimental and computational epitope mapping methods. The experimental methods include mutagenesis, X-ray crystallography, Nuclear Magnetic Resonance (NMR) spectroscopy, Hydroged deuterium eXchange Mass Spectrometry (HX-MS) and various competition binding methods. As each method relies on a unique principle the description of an epitope is intimately linked to the method by which it has been determined. Thus, the epitope for a given Ab/Ag pair will be defined differently depending on the epitope mapping method employed.

At its most detailed level, the epitope for the interaction between the Ag and the Ab can be defined by the spatial coordinates defining the atomic contacts present in the Ag—Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterium, e.g. distance between atoms in the Ab and the Ag. At a further, less detailed, level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as K3 or C-terminal residues characterized by having a heavy atom (i.e. a non-hydrogen atom) within a distance of 2-6 Å, such as 3 Å, such as 4 Å, such as 5 Å from a heavy atom in the Ab.

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid residue level, e.g. determined from an X-ray structure, are said to be identical if they contain the same set of amino acid residues. Epitopes are said to overlap if at least one amino acid residue is shared by the epitopes. Epitopes are said to be separate (unique) if no amino acid residue are shared by the epitopes.

Epitopes characterized by competition binding are said to be overlapping if the binding of corresponding Ab's are mutually exclusive, i.e. if the binding of one Ab excludes simultaneous binding of the other Ab. The epitopes are said to be separate (unique) if the Ag is able to accommodate binding of both corresponding Ab's simultaneously.

The definition of the term "paratope" is derived from the above definition of "epitope" by reversing the perspective. Thus, the term "paratope" refers to the area or region on the Ab to which an Ag specifically binds, i.e. to which it makes physical contact to the Ag.

In the context of an X-ray derived crystal structure defined by spatial coordinates of a complex between an Ab, e.g. a Fab fragment, and its Ag, the term paratope is herein, unless otherwise specified or contradicted by context, specifically defined as Ag residues characterized by having a heavy atom (i.e. a non-hydrogen atom) within a distance of 2-6 Å, such as 3 Å, such as 4 Å, such as 5 Å from a heavy atom in the C-terminal domain.

The epitope and paratope for a given antibody (Ab)/antigen (Ag) pair may be identified by routine methods. For example, the general location of an epitope may be determined by assessing the ability of an antibody to bind to different fragments or variant TFPI polypeptides. The specific amino acids within TFPI that make contact with an antibody (epitope) and the specific amino acids in an antibody that make contact with TFPI (paratope) may also be determined using routine methods, such as those described in the examples. For example, the antibody and target molecule may be combined and the Ab/Ag complex may be crystallised. The crystal structure of the complex may be determined and used to identify specific sites of interaction between the antibody and its target.

An antibody according to the current invention may bind to the same epitope, domain or portion of TFPI as the antibodies of the invention that are specifically disclosed herein. For example, other yet unidentified antibodies of the invention may be identified by comparing their binding to TFPI with that of the monoclonal antibodies, MuTFPI4F110, MuTFPI22F66 and MuTFPI22F71; or by comparing the function of yet unidentified antibodies with that of MuTFPI4F110, MuTFPI22F66 and MuTFPI22F71. Analyses and assays that may be used for the purpose of such identification include TFPI neutralizing assays such as: a FXa inhibition assay; an ELISA and binding interaction analyses, such as those described in the examples.

An antibody of the invention may bind an epitope comprising one or more amino acid residues, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 or 47 amino acid residues, such as 6-10 amino acid residues or 16-21 amino acid residues within the C terminal of full length TFPI, wherein said one or more amino acids have a relative accessibility of more than 40% when measured as described in the Examples. Thus, an antibody of the invention may bind an epitope comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 or 47 amino acid residues, such as 6-10 amino acid residues or 16-21 amino acid residues selected from the group consisting of amino acid residues 186-187, 190, 192-208, 213, 215-220, 225-228, 230-234, 236-237 and 240-276 of SEQ ID NO: 1.

An antibody of the invention may bind to an epitope that comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 or 47 amino acid residues, such as 6-10 amino acid residues or 16-21 amino acid residues, selected from the group consisting of P186, S187, L190, P192, A193, D194, R195, G196, L197, C198, R199, A200, N201, E202, N203, R204, F205, Y206, Y207, N208, K213, R215, P216, F217, K218, Y219, S220, N225, E226, N227, N228, T230, S231, K232, Q233, E234, L236, R237, K240, K241, G242, F243, I244, Q245, R246, I247, S248, K249, G250, G251, L252, I253, K254, T255, K256, R257, K258, R259, K260, K261, Q262, R263, V264, K265, I266, A267, Y268, E269, E270, I271, F272, V273, K274, N275 and M276 of SEQ ID NO: 1. For example, the antibody may bind to an epitope comprising 1, 2, 3, 4, 5, 6, 7, 8, 9, 10, 11, 12, 13, 14, 15, 16, 17, 18, 19, 20, 21, 22, 23, 24, 25 or 26 amino acid residues, selected from the group consisting of P186, S187, L190, P192, A193, D194, R195, G196, L197, C198, R199, A200, N201, E202, N203, R204, F205, Y206, Y207, N208, K213, R215, P216, F217, K218, Y219, S220, N225, E226, N227, N228, T230, S231, K232, Q233, E234, L236 and R237 of SEQ ID NO: 1. The antibody may bind to an epitope comprising 1, 2, 3, 4, 5, 6, 7, 8, 9, 10, 11, 12, 13, 14, 15, 16, 17, 18, 19, 20, 21, 22, 23, 24, 25 or 26 amino acid residues, such as 4-15 amino acid residues, such as 6-10 amino acid residues, selected from the group consisting of K240, K241, G242, F243, I244, Q245, R246, I247, S248, K249, G250, G251, L252, I253, K254, T255, K256, R257, K258, R259, K260, K261, Q262, R263, V264, K265, I266, A267, Y268, E269, E270, I271, F272, V273, K274, N275 and M276 of SEQ ID NO: 1.

An antibody of the invention may have the ability to compete with another antibody of the invention for binding to TFPI or another appropriate target as described herein. For example, an antibody of the invention may cross-compete with the antibodies identified as MuTFPI4F110, MuTFPI22F66 and MuTFPI22F71, described herein, for binding to TFPI, or to a suitable fragment or variant of TFPI that is bound by MuTFPI4F110, MuTFPI22F66 and MuTFPI22F71 antibodies. Such cross-competing antibodies can be identified based on their ability to cross-compete with a known antibody of the invention in standard binding assays. For example, SPR e.g. by using a Biacore™ system, ELISA assays or flow cytometry may be used to demonstrate cross-competition. Such cross-competition may suggest that the two antibodies bind to identical, overlapping or similar epitopes.

"Epitope binning" refers to the use of competitive binding assays to identify pairs of antibodies that are, or are not, capable of binding an antigen, such as TFPI, simultaneously, thereby identifying antibodies that bind to the same, or overlapping epitopes of TFPI. Families of antibodies (or bins) that have the same, or overlapping, binding specificity can then be used to help define specific epitopes on TFPI. Epitope binning experiments provide evidence that antigenically distinct epitopes are present. However, by themselves, they do not identify, or "map" the epitope to a specific amino acid sequence or location on TFPI. Competition for binding can be evaluated for any pair of antibodies or fragments. Favourable properties of a family (or bin) of antibodies can be correlated with binding to a specific epitope defined in terms of the antibody bin.

As explained above, TFPI downregulates blood coagulation. It does this by inhibiting the activity of FXa and by inhibiting the TF-FVIIa complex in the presence of FXa. The activity of TFPI that is inhibited by an antibody of the invention may be any of these activities or any downstream effect thereof. For example, an antibody of the invention may lead to an increase in blood coagulation, an increase in the presence or levels of FXa or an increased activity of TF-FVIIa. Preferably, an antibody of the invention reduces clotting time when contacted with (a) human FVIII deficient plasma or (b) human whole blood.

The measurement of TFPI activity may comprise assessing the activity of free TFPI in inhibiting coagulation or reducing clotting time in a blood sample. For example, such a method may comprise contacting TFPI with a sample of blood, or a blood product such as plasma or serum that comprises blood coagulation factors, under conditions in which coagulation should occur, and determining whether coagulation of the blood is inhibited or clotting time is reduced by the presence of the TFPI. The level of blood coagulation or clotting time in such a sample may then be compared to that in an equivalent sample in which a test antibody is also present. If the level of coagulation is increased or clotting time is reduced in the antibody sample, this suggests that the antibody is inhibiting the activity of TFPI in the sample.

Blood coagulation may be detected by looking for coagulation of the blood itself, of plasma, or for one or more characteristics of the coagulation cascade that lie downstream to the point of action of TFPI. For example, the method may assess levels of FXa or activation of TF-FVIIa in the sample.

Various other methods for assessing blood coagulation and clotting time are well known in the art. For example, any effect of an antibody on blood clotting time may be assessed using a dilute prothrombin time analysis (dPT analysis) as described in the examples. Briefly, human plasma is contacted with human thromboplastin. The time taken for the plasma to clot is measured in the presence and absence of the test antibody. A positive control may be used in such an analysis, such as addition of FVIIa (NovoSeven®), which would be expected to reduce clotting time. An antibody of the invention should be capable of reducing clotting time in such a method. Preferably, an antibody of the invention should be capable of reducing clotting time in a dose-dependent manner.

Thromboelastography (TEG) may be used to assess the kinetics of clot formation and fibrinolysis in samples of whole blood, such as in FVIII-deficient whole blood. The ability of an antibody to reduce clotting time or to stimulate blood coagulation may thus be similarly assessed in a whole blood sample by comparing the time taken for clot formation in the presence and absence of the antibody.

Methods to assess the functional effects of an antibody of the invention may thus be carried out in vitro. Such methods are preferably carried out on samples of human blood or plasma. Such samples may be normal human blood or plasma or may be deficient in, or supplemented with, one or more factors involved in blood coagulation. For example, these methods may be carried out using normal human whole blood, normal human plasma or FVIII-deficient plasma or whole blood. FVIII-deficient blood or plasma may be generated by contacting a suitable blood or plasma sample with neutralising anti-FVIII antibody. Such in vitro methods may be binding interaction analyses or TFPI neutralisation analyses, such as those described in the examples.

Once a suitable antibody has been identified and selected, the amino acid sequence of the antibody may be identified by methods known in the art. The genes encoding the antibody can be cloned using specific and/or degenerate primers. The antibody may be recombinantly produced by routine methods.

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

A polynucleotide of the invention may comprise a sequence which encodes a VH or VL amino acid sequence as described above. For example, a polynucleotide of the invention may encode a polypeptide comprising any one or more of the sequences selected from the group consisting of: SEQ ID NOs: 5, 7, 9, 11, 13 and 15; or variants or fragments thereof.

Polynucleotides of the invention may be synthesised according to methods well known in the art, as described by way of example in Sambrook et al (1989, Molecular Cloning—a laboratory manual; Cold Spring Harbor Press).

The nucleic acid molecules of the present invention may be provided in the form of an expression cassette which includes control sequences, signal peptide sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers, signal peptide sequences and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express an antibody of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for an antibody of the invention include mammalian HEK293, CHO, BHK, NSO and human retina cells. Preferably the cell line selected will be one which is not only stable, but also allows for mature glycosylation and cell surface expression of a polypeptide.

In another aspect, the present invention provides compositions and formulations comprising molecules of the invention, such as the antibodies, polynucleotides, vectors and cells described herein. For example, the invention provides a pharmaceutical composition that comprises one or more antibodies of the invention, formulated together with a pharmaceutically acceptable carrier.

Accordingly, one object of the invention is to provide a pharmaceutical formulation comprising such an antibody which is present in a concentration from 1 mg/ml to 200 mg/ml, and wherein said formulation has a pH from 2.0 to 10.0. The formulation may further comprise a buffer system, preservative(s), tonicity agent(s), chelating agent(s), stabilizers and surfactants. The use of preservatives, isotonic agents, chelating agents, stabilizers and surfactants in pharmaceutical compositions is well-known to the skilled person. Reference may be made to Remington: *The Science and Practice of Pharmacy*, 19$^{th}$ edition, 1995.

In one embodiment, the pharmaceutical formulation is an aqueous formulation. Such a formulation is typically a solution or a suspension. The terms "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration of 1-200 mg/ml, and wherein said formulation has a pH from about 2.0 to about 10.0.

An antibody or a pharmaceutical formulation of the invention may be used to treat a subject with a coagulopathy.

As used herein, the term "subject" includes any human patient, or non-human vertebrate, with a coagulopathy.

The term "treatment", as used herein, refers to the medical therapy of any human or other vertebrate subject in need thereof. Said subject is expected to have undergone physical examination by a medical practitioner or a veterinary medical practitioner, who has given a tentative or definitive diagnosis which would indicate that the use of said specific treatment is beneficial to the health of said human or other vertebrate. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

The term "coagulopathy", as used herein, refers to an increased haemorrhagic tendency which may be caused by any qualitative or quantitative deficiency of any pro-coagulative component of the normal coagulation cascade, or any upregulation of fibrinolysis. Such coagulopathies may be congenital and/or acquired and/or iatrogenic and are identified by a person skilled in the art.

Non-limiting examples of congenital hypocoagulopathies are haemophilia A, haemophilia B, Factor VII deficiency, Factor XI deficiency, von Willebrand's disease and thrombocytopenias such as Glanzmann's thombasthenia and Bernard-Soulier syndrome. Haemophilia A with "inhibitors" (that is, allo-antibodies against factor VIII) and haemophilia B with "inhibitors" (that is, allo-antibodies against factor IX) are non-limiting examples of coagulopathies that are partly congenital and partly acquired.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exacerbate this situation. Said haemorrhage may be from any part of the body.

A non-limiting example of an iatrogenic coagulopathy is an overdosage of anticoagulant medication—such as heparin, aspirin, warfarin and other platelet aggregation inhibitors—that may be prescribed to treat thromboembolic disease. A second, non-limiting example of iatrogenic coagulopathy is that which is induced by excessive and/or inappropriate fluid therapy, such as that which may be induced by a blood transfusion.

In one embodiment of the current invention, haemorrhage is associated with haemophilia A or B. In another embodiment, haemorrhage is associated with haemophilia A or B with acquired inhibitors. In another embodiment, haemorrhage is associated with thrombocytopenia. In another embodiment, haemorrhage is associated with von Willebrand's disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intraaurally or intraocularly. In another embodiment, haemorrhage is associated with anticoagulant therapy.

The use of an antibody or formulation of the invention may significantly reduce blood loss in subjects in need thereof. The use of said antibody or formulation may significantly reduce bleeding time. Thus, the invention is also the use of an antibody that is capable of binding the C-terminal of TFPI, for the treatment of a subject with a coagulopathy. Furthermore, the invention is a method of treating a subject in need thereof with a monoclonal antibody that is capable of binding to the C-terminal of TFPI. Use of said monoclonal antibody of the invention will, preferably, reduce in vivo clotting time without causing transient thrombocytopaenia.

An antibody of the invention may be administered parenterally, such as intravenously, such as intramuscularly, such as subcutaneously. Alternatively, an antibody of the invention may be administered via a non-parenteral route, such as perorally or topically. An antibody of the invention may be administered prophylactically. An antibody of the invention may be administered therapeutically (on demand).

A suitable dosage of an antibody of the invention may be determined by a skilled medical or veterinary medical practitioner. A suitable dose of an antibody of the invention may be in the range of from about 0.1 µg/kg to about 100 mg/kg body weight of the patient to be treated.

Furthermore, antibodies of the invention may be co-administered with one or more other therapeutic agents or formulations. The other agent may be an agent that enhances haemostasis, such as a Factor VIIa polypeptide, a Factor VIII polypeptide or a Factor IX polypeptide. The other agent may be intended to treat other symptoms or conditions of the patient. For example, the other agent may be an analgesic, an immunosuppressant or an anti-inflammatory agent. The other agent may be a monoclonal antibody, such as one of those disclosed in international patent application WO2010072691.

Co-administration of an antibody of the invention and said one or more other agents may be achieved in a number of different ways. In one embodiment, an antibody of the invention and the other agent may be administered together in a single composition. In another embodiment, an antibody of the invention and the other agent may be administered separately but as part of a combined therapy. For example, an antibody of the invention may be administered before, after, or concurrently with the other agent. In its broadest sense, co-administration according to the current invention refers to an antibody of the invention and the other agent being present in human blood at the same time, irrespective of the time when the two or more agents were administered. Thus, an antibody of the invention may be present in the blood at the same time as an exogenous FVIIa polypeptide, FVIII polypeptide or FIX polypeptide.

The term "Factor VII(a)" herein encompasses the uncloven zymogen, Factor VII (FVII), as well as the cloven and thus activated protease, Factor VIIa (FVIIa). "Factor VII(a)" includes natural allelic variants of FVII(a) that may exist and occur from one individual to another. A wild type human Factor VIIa sequence is provided in SEQ ID NO: 19, as well as in Proc Natl Acad Sci USA 1986; 83:2412-2416.

```
Wild type human coagulation Factor VII(a) (SEQ ID NO. 19):
ANAFLγγLRPGSLγRγCKγγQCSFγγARγIFKDAγRTKLFWISYSDGDQCASSPCQNGGSCKDQLQSYICF

CLPAFEGRNCETHKDDQLICVNENGGCEQYCSDHTGTKRSCRCHEGYSLLADGVSCTPTVEYPCGKI

PILEKRNASKPQGRIVGGKVCPKGECPWQVLLLVNGAQLCGGTLINTIWVVSAAHCFDKIKNWRNLI

AVLGEHDLSEHDGDEQSRRVAQVIIPSTYVPGTTNHDIALLRLHQPVVLTDHVVPLCLPERTFSERTLA

FVRFSLVSGWGQLLDRGATALELMVLNVPRLMTQDCLQQSRKVGDSPNITEYMFCAGYSDGSKDSC

KGDSGGPHATHYRGTWYLTGIVSWGQGCATVGHFGVYTRVSQYIEWLQKLMRSEPRPGVLLRAPFP
```

Wild type FVII consists of 406 amino acid residues and is composed of four domains as defined by homology. There is an N-terminal Gla domain followed by two epidermal growth factor (EGF)-like domains and a C-terminal serine protease domain. FVII circulates in plasma as a single-chain molecule. Upon activation to activated FVII (FVIIa), the molecule is cloven between residues Arg152 and Ile153, resulting in a two-chain protein held together by a disulphide bond. The light chain contains the Gla and EGF-like domains, whereas the heavy chain is the protease domain. FVIIa requires binding to its cell-surface co-factor tissue factor (TF) to become biologically active.

Factor VII(a) may be plasma-derived or recombinantly produced, using well known methods of production and purification. The degree and location of glycosylation, gamma-carboxylation and other post-translational modifications may vary depending on the chosen host cell and its growth conditions. In SEQ ID NO. 19, "γ" (gamma) represents represents gamma-carboxylated Glu ('E') remains. The term "Factor VII(a) polypeptide" herein refers to wild type Factor VIIa molecules as well as FVII(a) variants, FVII(a) derivatives and FVII(a) conjugates. Such variants, derivatives and conjugates may exhibit substantially the same, or improved, biological activity relative to wild-type human Factor VIIa.

The term "FVII(a) variant", as used herein, is intended to designate Factor FVII having the sequence of SEQ ID NO: 19, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "analogue" or "analogues" within this definition still have FVII activity in its activated form. In one embodiment a variant is at least 90% identical with the sequence of SEQ ID NO: 19. In another embodiment a variant is at least 95% identical with the sequence of SEQ ID NO: 19. As used herein, any reference to a specific position refers to the corresponding position in SEQ ID NO: 19.

Non-limiting examples of FVII(a) variants that have substantially the same or increased proteolytic activity compared to recombinant wild type human Factor VII(a) include those disclosed in WO 01/83725, WO 02/22776, WO 02/077218, WO 03/027147, WO 03/037932, WO 04/029090, WO 05/024006, and EP 05108713.8, U.S. Pat. No. 7,173,000 B2; and JP4451514 B2.

The term "Factor VII(a) derivative" as used herein, is intended to designate a FVII poly-peptide that exhibits substantially the same or improved biological activity relative to wild-type Factor VIIa, in which one or more of the amino acids of the parent peptide have been genetically and/or chemically and/or enzymatically modified, such as by alkylation, glycosylation, PEGylation, acylation, ester formation, disulfide bond formation, or amide formation.

The term "PEGylated human Factor VII(a)" refers to a human Factor VII(a) polypeptide, to which a PEG molecule has been conjugated. Such a PEG molecule may be attached to any part of the Factor VIIa polypeptide, including any amino acid residue or carbohydrate moiety of the Factor VIIa polypeptide. This includes but is not limited to PEGylated human Factor VIIa, cysteine-PEGylated human Factor VIIa and variants thereof. Non-limiting examples of Factor VII derivatives includes glycoPEGylated FVII(a) derivatives as disclosed in WO 03/031464 and WO 04/099231 and WO 02/077218, The term "cysteine-PEGylated human Factor VII(a)" refers to a Factor VII(a) polypeptide in which a PEG molecule is conjugated to a sulfhydryl group of a cysteine that has been introduced into said human Factor VIIa.

The term "improved biological activity" refers to FVII(a) polypeptides that exhibit i) substantially the same or increased proteolytic activity compared to recombinant wild type human Factor VIIa in the presence and/or absence of tissue factor or ii) to FVII(a) polypeptides with substantially the same or increased TF affinity compared to recombinant wild type human Factor VIIa or iii) to FVII(a) polypeptides with substantially the same or increased half life in plasma compared to recombinant wild type human Factor VIIa, or iv) to FVII(a) polypeptides with substantially the same or increased affinity for the activated platelet. The activity of FVIIa polypeptides may be tested using, for example, the in vitro hydrolysis assay or the in vitro proteolysis assay, as described in the examples.

"Factor VIII" or "FVIII" herein refers to a human plasma glycoprotein that is a member of the intrinsic coagulation pathway and is essential to blood coagulation. "Native FVIII" is the human FVIII molecule derived from the full length sequence as shown in SEQ ID NO: 20 (amino acid 1-2332). The terms "Factor VIII(a)" and "FVIII(a)" herein include both FVIII and FVIIIa. "FVIII(a)" includes natural allelic variants of FVIII(a) that may exist and occur from one individual to another. FVIII(a) may be plasma-derived or recombinantly produced, using well known methods of production and purification. The degree and location of glycosylation, tyrosine sulfation and other post-translation modifications may vary, depending on the chosen host cell and its growth conditions.

Factor VIII (FVIII) is a large, complex glycoprotein that is primarily produced by hepatocytes. FVIII consists of 2351 amino acids, including a signal peptide, and contains several distinct domains as defined by homology. There are three A-domains, a unique B-domain, and two C-domains. The domain order can be listed as NH2-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC). Small acidic regions C-terminal of the A1 (the $a_1$ region) and A2 (the $a_2$ region) and N-terminal of the A3 domain (the $a_3$ region) play important roles in its interaction with other coagulation proteins, including thrombin and von Willebrand factor (vWF or VWF), the carrier protein for FVIII.

Endogenous FVIII molecules circulate in vivo as a pool of molecules with B domains of various sizes, the shortest having C-terminal at position 740, i.e. at the C-terminal of A2-$a_2$. These FVIII molecules with B-domains of different length all have full procoagulant activity. Upon activation with thrombin, FVIII is cloven C-terminal of A1-$a_1$ at position 372, C-terminal of A2-$a_2$ at position 740, and between $a_3$ and A3 at position 1689, the latter cleavage releasing the $a_3$ region with concomitant loss of affinity for VWF. The activated FVIII molecule is termed FVIIIa. The activation allows interaction of FVIIIa with phospholipid surfaces like activated platelets and activated factor IX (FIXa), i.e. the tenase complex is formed, allowing efficient activation of factor X (FX).

FVIII molecules/variants may be B domain-truncated FVIII molecules wherein the remaining domains correspond closely to the sequences as set forth in amino acid numbers 1-740 and 1649-2332 of SEQ ID NO: 20. In such variants, as well as in FVIII derived from the full-length sequence, mutations may be introduced in order to, for example, reduce vWF binding capacity. Amino acid modifications, such as substitutions and deletions, may be introduced into the molecule in order to modify the binding capacity of FVIII with various other components such as LRP, various receptors, other coagulation factors, cell surfaces, introduction and/or abolishment of glycosylation sites, etc. Other mutations that do not abolish FVIII activity may also be accommodated in a FVIII molecule/variant according to the present invention.

FVIII molecules that are administered according to the present invention are capable of functioning in the coagulation cascade in a manner that is functionally similar, or equivalent, to FVIII, inducing the formation of FXa via interaction with FIXa on an activated platelet and supporting the formation of a blood clot. FVIII activity can be assessed in vitro using techniques well known in the art. Clot analyses, FX activation assays (often termed chromogenic assays), thrombin generation assays and whole blood thromboelastography are examples of such in vitro techniques. FVIII molecules according to the present invention have FVIII activity that is at least about 10%, at least about 20%, at least about 30%, at least about 40%, at least about 50%, at least about 60%, at least about 70%, at least about 80%, at least about 90%, 100% or even more than 100% of that of native human FVIII.

The B domain in FVIII spans amino acids 741-1648 of SEQ ID NO: 20. The B domain is cloven at several different sites, generating large heterogeneity in circulating plasma FVIII molecules. The exact function of the heavily glycosylated B domain is unknown. What is known is that the B domain is dispensable for FVIII activity in the coagulation cascade. Recombinant FVIII is thus frequently produced in the form of B domain-deleted/truncated variants.

Endogenous full length FVIII is synthesized as a single-chain precursor molecule. Prior to secretion, the precursor is cloven into the heavy chain and the light chain. Recombinant B domain-deleted FVIII can be produced by means of two different strategies. Either the heavy chain without the B-domain and the light chain are synthesized individually as two different polypeptide chains (two-chain strategy) or the B domain-deleted FVIII is synthesized as a single precursor polypeptide chain (single-chain strategy) that is cloven into the heavy and light chains in the same way as the full-length FVIII precursor.

"Factor IX(a)" includes natural allelic variants of FIX(a) that may exist and occur from one individual to another. Factor IX(a) may be plasma-derived or recombinantly produced using well known methods of production and purification. The degree and location of glycosylation, gamma-carboxylation and other post-translation modifications may vary depending on the chosen host cell and its growth conditions. Unless otherwise specified or indicated, Factor IX means any functional human Factor IX protein molecule in its normal role in coagulation, including any fragment, analogue and derivative thereof.

One example of a "wild type FIX" is the full length human FIX molecule, as shown in SEQ ID NO: 21.

```
Wild type human coagulation Factor IX (SEQ ID NO: 21):
YNSGKLγγFVQGNLγRγCMγγKCSFγγARγVFγNTγRTTγFWKQYVDGDQCESNPCLNGGSCKDDINSYE

CWCPFGFEGKNCELDVTCNIKNGRCEQFCKNSADNKVVCSCTEGYRLAENQKSCPAVPFPCGRVSV

SQTSKLTRAEAVFPDVDYVNSTEAETILDNITQSTQSFNDFTRVVGGEDAKPGQFPWQVVLNGKVDA

FCGGSIVNEKWIVTAAHCVETGVKITVVAGEHNIEETEHTEQKRNVIRIIPHHNYNAAINKYNHDIALL

ELDEPLVLNSYVTPICIADKEYTNIFLKFGSGYVSGWGRVFHKGRSALVLQYLRVPLVDRATCLRSTKF

TIYNNMFCAGFHEGGRDSCQGDSGGPHVTEVEGTSFLTGIISWGEECAMKGKYGIYTKVSRYVNWI

KEKTKLT
```

In a B domain-deleted FVIII precursor polypeptide, produced by the single-chain strategy, the heavy and light chain moieties are often separated by a linker. To minimize the risk of introducing immunogenic epitopes in the B domain-deleted FVIII, the sequence of the linker is preferably derived from the FVIII B-domain. As a minimum, the linker must comprise a recognition site for the protease that cleaves the B domain-deleted FVIII precursor polypeptide into the heavy and light chain. In the B domain of full length FVIII, amino acid 1644-1648 constitutes this recognition site. The thrombin cleavage site leading to removal of the linker on activation of B domain-deleted FVIII is located in the heavy chain. Thus, the size and amino acid sequence of the linker is unlikely to influence its removal from the remaining FVIII molecule by thrombin activation. Deletion/truncation of the B domain is an advantage for production of FVIII. Nevertheless, parts of the B domain can be included in the linker without reducing the productivity. The negative effect of the B domain on productivity has not been attributed to any specific size or sequence of the B domain.

Factor IXa (FIXa) is a trypsin-like serine protease that serves a key role in haemostasis by generating, as part of the tenase complex, most of the factor Xa required to support proper thrombin formation during coagulation (reviewed in (Hoffman and Monroe, III 2001)).

Factor IX (FIX) is a vitamin K-dependent coagulation factor with structural similarities to factor VII, prothrombin, factor X, and protein C. The circulating zymogen form consists of 415 amino acids divided into four distinct domains comprising an N-terminal γ-carboxyglutamic acid-rich (Gla) domain, two EGF domains and a C-terminal trypsin-like serine protease domain. Activation of FIX occurs by limited proteolysis at $Arg^{145}$-$Ala^{146}$ and $Arg^{180}$-$Val^{181}$ releasing a 35-aa fragment, the so-called activation peptide (Schmidt and Bajaj 2003). The activation peptide is heavily glycosylated, containing two N-linked and up to four O-linked glycans.

"Factor IX" or "FIX", as used herein, refers to a human plasma Factor IX glycoprotein that is a member of the intrinsic coagulation pathway and is essential to blood coagulation.

In SEQ ID NO: 21, "γ" represents gamma-carboxylated Glu ('E') remains. In fully gamma-carboxylated FIX, the first 12 Glu residues are gamma-carboxylated, but there are variants, especially in the case of recombinant FIX, in which less gamma-carboxylation takes place. Note, also, that a dimorphism occurs in FIX at position 148, which can be either Ala or Thr (see McGraw et al. (1985) PNAS, 82:2847). Both are "wild type" FIX.

The terms "FIX analogue", as used herein, is intended to designate Factor FIX having the sequence of SEQ ID NO: 21, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "analogue" or "analogues" within this definition still have FIX activity in its activated form. In one embodiment a variant is at least 90% identical with the sequence of of SEQ ID NO: 21. In a further embodiment a variant is at least 95% identical with the sequence of of SEQ ID NO: 21. As used herein any reference to a specific positions refers to the corresponding position in SEQ ID NO: 21.

Unless otherwise specified, factor IX domains include the following amino acid residues: Gla domain being the region from reside Tyr1 to residue Lys43; EGF1 being the region from residue Gln44 to residue Leu84; EGF2 being the region from residue Asp85 to residue Arg145; the Activation Peptide being the region from residue Ala146 to residue Arg180; and the Protease Domain being the region from residue Val181 to Thr414. The light chain refers to the region encompassing the Gla domain, EGF1 and EGF2, while the heavy chain refers to the Protease Domain.

The clotting activity of procoagulant agents such as FVIIa polypeptide, a FVIII polypeptide or a Factor IX polypeptide may be determined using clotting assays that are known to the person skilled in the art, such as those described in the Examples.

The time at which antibodies of the invention are to be co-administered with a second agent, such as a Factor VIIa polypeptide, a Factor VIII polypeptide or a Factor IX polypeptide, may be determined by the skilled medical or veterinary medical practitioner.

Following is a non-limiting list of embodiments of the present invention:

Embodiment 1: An antibody that is capable of specifically binding the C-terminal of full length TFPI.

Embodiment 1a: The antibody according to embodiment 1, wherein said C-terminal is amino acids 186-276 of human TFPI (SEQ ID NO: 1).

Embodiment 1b: The antibody according to any one of embodiments 1 or 1a, which is a monoclonal antibody.

Embodiment 2: The antibody according to any one of embodiments 1-1b, wherein the epitope of said antibody comprises one or more amino acid residues selected from the group consisting of P186, S187, L190, P192, A193, D194, R195, G196, L197, C198, R199, A200, N201, E202, N203, R204, F205, Y206, Y207, N208, K213, R215, P216, F217, K218, Y219, S220, N225, E226, N227, N228, T230, S231, K232, Q233, E234, L236, R237, K240, K241, G242, F243, I244, Q245, R246, I247, S248, K249, G250, G251, L252, I253, K254, T255, K256, R257, K258, R259, K260, K261, Q262, R263, V264, K265, I266, A267, Y268, E269, E270, I271, F272, V273, K274, N275 and M276 of SEQ ID NO: 1.

Embodiment 2a: The antibody according to any one of embodiments 1-1b, wherein the epitope of said antibody comprises one or more amino acid residues selected from the group consisting of P186, S187, L190, P192, A193, D194, R195, G196, L197, C198, R199, A200, N201, E202, N203, R204, F205, Y206, Y207, N208, K213, R215, P216, F217, K218, Y219, S220, N225, E226, N227, N228, T230, S231, K232, Q233, E234, L236, R237, K240, K241, G242 and F243 of SEQ ID NO: 1.

Embodiment 3: The antibody according to any one of embodiments 1-1b, wherein the epitope of said antibody comprises one or more amino acid residues selected from the group consisting of P186, S187, L190, P192, A193, D194, R195, G196, L197, C198, R199, A200, N201, E202, N203, R204, F205, Y206, Y207, N208, K213, R215, P216, F217, K218, Y219, S220, N225, E226, N227, N228, T230, S231, K232, Q233, E234, L236 and R237 of SEQ ID NO: 1.

Embodiment 4: The antibody according to any one of embodiments 1-1b, wherein the epitope of said antibody comprises one or more amino acid residues selected from the group consisting of K240, K241, G242, F243, I244, Q245, R246, I247, S248, K249, G250, G251, L252, I253, K254, T255, K256, R257, K258, R259, K260, K261, Q262, R263, V264, K265, I266, A267, Y268, E269, E270, I271, F272, V273, K274, N275 and M276 of SEQ ID NO: 1.

Embodiment 5: The antibody according to any one of embodiments 1-4, wherein the heavy chain of said antibody comprises a CDR1 sequence of amino acids 31 to 35 (SYYMY) of SEQ ID NO: 5, wherein one of these amino acids may be substituted by a different amino acid.

Embodiment 6: The antibody according to any one of embodiments 1-5, wherein the heavy chain of said antibody comprises a CDR2 sequence of amino acids 50-66 (EINPSNGDTNLNEKFKS) of SEQ ID NO: 5, wherein one, two or three of these amino acids may be substituted by a different amino acid.

Embodiment 7: The antibody according to any one of embodiments 1-6, wherein the heavy chain of said antibody comprises a CDR3 sequence of amino acids 99-107 (WDRFDGFVY) of SEQ ID NO: 5, wherein one or two of these amino acids may be substituted by a different amino acid.

Embodiment 8: The antibody according to any one of embodiments 1-4, wherein the heavy chain of said antibody comprises a CDR1 sequence of amino acids 31-35 (GYPMN) of SEQ ID NO: 9, wherein one of these amino acids may be substituted by a different amino acid.

Embodiment 9: The antibody according to any one of embodiments 1-4 and 8, wherein the heavy chain of said antibody comprises a CDR2 sequence of amino acids 50-66 (LINPYNGDTTFNQKFKG) of SEQ ID NO: 9, wherein one, two or three of these amino acids may be substituted by a different amino acid.

Embodiment 10: The antibody according to any one of embodiments 1-4 and 8-9, wherein the heavy chain of said antibody comprises a CDR3 sequence of amino acids 99-106 (GTYEYVDY) of SEQ ID NO: 9, wherein one or two of these amino acids may be substituted by a different amino acid.

Embodiment 11: The antibody according to any one of embodiments 1-4, wherein the heavy chain of said antibody comprises a CDR1 sequence of amino acids 31-35 (TYWIH) of SEQ ID NO: 13, wherein one of these amino acids may be substituted by a different amino acid.

Embodiment 12: The antibody according to any one of embodiments 1-4 and 11, wherein the heavy chain of said antibody comprises a CDR2 sequence of amino acids 50-66 (AIDPGNSDATYSQKFKD) of SEQ ID NO: 13, wherein one, two or three of these amino acids may be substituted by a different amino acid.

Embodiment 13: The antibody according to any one of embodiments 1-4 and 11-12, wherein the heavy chain of said antibody comprises a CDR3 sequence of amino acids 99-111 (EVYYGYDGDYFDY) of SEQ ID NO: 13, wherein one, two or three of these amino acids may be substituted by a different amino acid.

Embodiment 14: The antibody according to any one of embodiments 1-7, wherein the light chain of said antibody comprises a CDR1 sequence of amino acids 24-34 (IISTNID-DDIN) of SEQ ID NO: 7, wherein one, two or three of these amino acids may be substituted with a different amino acid.

Embodiment 15: The antibody according to any one of embodiments 1-7 and 14, wherein the light chain of said antibody comprises a CDR2 sequence of amino acids 50-56 (EGNTLRP) of SEQ ID NO: 7, wherein one of these amino acids may be substituted with a different amino acid.

Embodiment 16: The antibody according to any one of embodiments 1-7 and 14-15, wherein the light chain of said antibody comprises a CDR3 sequence of amino acids 89-97 (LQSDDLPYT) of SEQ ID NO: 7, wherein one or two of these amino acids may be substituted with a different amino acid.

Embodiment 17: The antibody according to any one of embodiments 1-4 and 8-10, wherein the light chain of said antibody comprises a CDR1 sequence of amino acids 24-33 (SASSSVFYMH) of SEQ ID NO: 11, wherein one, two or three of these amino acids may be substituted with a different amino acid.

Embodiment 18: The antibody according to any one of embodiments 1-4, 8-10 and 17, wherein the light chain of said antibody comprises a CDR2 sequence of amino acids 49-55 (DTSILSS) of SEQ ID NO: 11, wherein one of these amino acids may be substituted with a different amino acid.

Embodiment 19: The antibody according to any one of embodiments 1-4, 8-10 and 17-18, wherein the light chain of said antibody comprises a CDR3 sequence of amino acids 88-96 (QQWSSYPLT) of SEQ ID NO: 11, wherein one or two of these amino acids may be substituted with a different amino acid.

Embodiment 20: The antibody according to any one of embodiments 1-4 and 11-13, wherein the light chain of said antibody comprises a CDR1 sequence of amino acids 24-38 (RASESVSVHGTHLMH) of SEQ ID NO: 15, wherein one, two or three of these amino acids may be substituted with a different amino acid.

Embodiment 21: The antibody according to any one of embodiments 1-4, 11-13 and 20, wherein the light chain of said antibody comprises a CDR2 sequence of amino acids 54-60 (AASKLES) of SEQ ID NO: 15, wherein one of these amino acids may be substituted with a different amino acid.

Embodiment 22: The antibody according to any one of embodiments 1-4, 11-13 and 20-21, wherein the light chain of said antibody comprises a CDR3 sequence of amino acids 93-101 (QQSIGDPWT) of SEQ ID NO: 15, wherein one or two of these amino acids may be substituted with a different amino acid.

Embodiment 23: The antibody according to any one of embodiments 1-4, wherein the heavy chain of said antibody comprises:
- a CDR1 sequence of amino acids 31 to 35 (SYYMY) of SEQ ID NO: 5, wherein one of these amino acids may be substituted by a different amino acid; and/or
- a CDR2 sequence of amino acids 50-66 (EINPSNGDTNL-NEKFKS) of SEQ ID NO: 5, wherein one, two or three of these amino acids may be substituted by a different amino acid; and/or
- a CDR3 sequence of amino acids 99-107 (WDRFDGFVY) of SEQ ID NO: 5, wherein one or two of these amino acids may be substituted by a different amino acid.

Embodiment 24: The antibody according to any one of embodiments 1-4, wherein the heavy chain of said antibody comprises:
- a CDR1 sequence of amino acids 31-35 (GYPMN) of SEQ ID NO: 9, wherein one of these amino acids may be substituted by a different amino acid; and/or
- a CDR2 sequence of amino acids 50-66 (LINPYNGDT-TFNQKFKG) of SEQ ID NO: 9, wherein one, two or three of these amino acids may be substituted by a different amino acid; and/or
- a CDR3 sequence of amino acids 99-106 (GTYEYVDY) of SEQ ID NO: 9, wherein one or two of these amino acids may be substituted by a different amino acid.

Embodiment 25: The antibody according to any one of embodiments 1-4, wherein the heavy chain of said antibody comprises:
- a CDR1 sequence of amino acids 31-35 (TYWIH) of SEQ ID NO: 13, wherein one of these amino acids may be substituted by a different amino acid; and/or
- a CDR2 sequence of amino acids 50-66 (AIDPGNS-DATYSQKFKD) of SEQ ID NO: 13, wherein one, two or three of these amino acids may be substituted by a different amino acid; and/or
- a CDR3 sequence of amino acids 99-111 (EVYYGYDGDYFDY) of SEQ ID NO: 13, wherein one or two of these amino acids may be substituted by a different amino acid.

Embodiment 26: The antibody according to any one of embodiments 1-4, wherein the light chain of said antibody comprises:
- a CDR1 sequence of amino acids 24-34 (IISTNIDDDIN) of SEQ ID NO: 7, wherein one, two or three of these amino acids may be substituted with a different amino acid; and/or
- a CDR2 sequence of amino acids 50-56 (EGNTLRP) of SEQ ID NO: 7, wherein one or two of these amino acids may be substituted with a different amino acid; and/or
- a CDR3 sequence of amino acids 89-97 (LQSDDLPYT) of SEQ ID NO: 7, wherein one or two of these amino acids may be substituted with a different amino acid.

Embodiment 27: The antibody according to any one of embodiments 1-4, wherein the light chain of said antibody comprises:
- a CDR1 sequence of amino acids 24-33 (SASSSVFYMH) of SEQ ID NO: 11, wherein one, two or three of these amino acids may be substituted with a different amino acid; and/or
- a CDR2 sequence of amino acids 49-55 (DTSILSS) of SEQ ID NO: 11, wherein one or two of these amino acids may be substituted with a different amino acid; and/or
- a CDR3 sequence of amino acids 88-96 (QQWSSYPLT) of SEQ ID NO: 11, wherein one or two of these amino acids may be substituted with a different amino acid.

Embodiment 28: The antibody according to any one of embodiments 1-4, wherein the light chain of said antibody comprises:
- a CDR1 sequence of amino acids 24-38 (RASESVSVH-GTHLMH) of SEQ ID NO: 15, wherein one, two or three of these amino acids may be substituted with a different amino acid; and/or
- a CDR2 sequence of amino acids 54-60 (AASKLES) of SEQ ID NO: 15, wherein one or two of these amino acids may be substituted with a different amino acid; and/or
- a CDR3 sequence of amino acids 93-101 (QQSIGDPWT) of SEQ ID NO: 15, wherein one or two of these amino acids may be substituted with a different amino acid.

Embodiment 29: The antibody according to any one of embodiments 1-4, wherein the heavy chain of said antibody comprises:
- a CDR1 sequence of amino acids 31 to 35 (SYYMY) of SEQ ID NO: 5, wherein one of these amino acids may be substituted by a different amino acid; and/or
- a CDR2 sequence of amino acids 50-66 (EINPSNGDTNL-NEKFKS) of SEQ ID NO: 5, wherein one, two or three of these amino acids may be substituted by a different amino acid; and/or
- a CDR3 sequence of amino acids 99-107 (WDRFDGFVY) of SEQ ID NO: 5, wherein one or two of these amino acids may be substituted by a different amino acid.
and wherein the light chain of said antibody comprises:
- a CDR1 sequence of amino acids 24-34 (IISTNIDDDIN) of SEQ ID NO: 7, wherein one, two or three of these amino acids may be substituted with a different amino acid; and/or
- a CDR2 sequence of amino acids 50-56 (EGNTLRP) of SEQ ID NO: 7, wherein one or two of these amino acids may be substituted with a different amino acid; and/or
- a CDR3 sequence of amino acids 89-97 (LQSDDLPYT) of SEQ ID NO: 7, wherein one or two of these amino acids may be substituted with a different amino acid.

Embodiment 30: The antibody according to any one of embodiments 1-4, wherein the heavy chain of said antibody comprises:
- a CDR1 sequence of amino acids 31-35 (GYPMN) of SEQ ID NO: 9, wherein one of these amino acids may be substituted by a different amino acid; and/or
- a CDR2 sequence of amino acids 50-66 (LINPYNGDT-TFNQKFKG) of SEQ ID NO: 9, wherein one, two or three of these amino acids may be substituted by a different amino acid; and/or a CDR3 sequence of amino acids 99-106 (GTYEYVDY) of SEQ ID NO: 9, wherein one or two of these amino acids may be substituted by a different amino acid.

and wherein the light chain of said antibody comprises:

a CDR1 sequence of amino acids 24-33 (SASSSVFYMH) of SEQ ID NO: 11, wherein one, two or three of these amino acids may be substituted with a different amino acid; and/or a CDR2 sequence of amino acids 49-55 (DTSILSS) of SEQ ID NO: 11, wherein one or two of these amino acids may be substituted with a different amino acid; and/or a CDR3 sequence of amino acids 88-96 (QQWSSYPLT) of SEQ ID NO: 11, wherein one or two of these amino acids may be substituted with a different amino acid.

Embodiment 31: The antibody according to any one of embodiments 1-4, wherein the heavy chain of said antibody comprises:

a CDR1 sequence of amino acids 31-35 (TYWIH) of SEQ ID NO: 13, wherein one of these amino acids may be substituted by a different amino acid; and/or a CDR2 sequence of amino acids 50-66 (AIDPGNS-DATYSQKFKD) of SEQ ID NO: 13, wherein one, two or three of these amino acids may be substituted by a different amino acid; and/or a CDR3 sequence of amino acids 99-111 (EVYYGYDGDYFDY) of SEQ ID NO: 13, wherein one or two of these amino acids may be substituted by a different amino acid.

and wherein the light chain of said antibody comprises:

a CDR1 sequence of amino acids 24-38 (RASESVSVH-GTHLMH) of SEQ ID NO: 15, wherein one, two or three of these amino acids may be substituted with a different amino acid; and/or a CDR2 sequence of amino acids 54-60 (AASKLES) of SEQ ID NO: 15, wherein one or two of these amino acids may be substituted with a different amino acid; and/or a CDR3 sequence of amino acids 93-101 (QQSIGDPWT) of SEQ ID NO: 15, wherein one or two of these amino acids may be substituted with a different amino acid.

Embodiment 32: The antibody according to any one of embodiments 5-31, wherein said amino acid substitution is a conservative substitution.

Embodiment 33: The antibody according to any one of embodiments 1-4, wherein the heavy chain comprises:

a CDR1 sequence of amino acids 31 to 35 (SYYMY) of SEQ ID NO: 5 and/or a CDR2 sequence of amino acids 50-66 (EINPSNGDTNL-NEKFKS) of SEQ ID NO: 5 and/or a CDR3 sequence of amino acids 99-107 (WDRFDGFVY) of SEQ ID NO: 5;

and wherein the light chain of said antibody comprises:

a CDR1 sequence of amino acids 24-34 (IISTNIDDDIN) of SEQ ID NO: 7 and/or a CDR2 sequence of amino acids 50-56 (EGNTLRP) of SEQ ID NO: 7 and/or a CDR3 sequence of amino acids 89-97 (LQSDDLPYT) of SEQ ID NO: 7.

Embodiment 34: The antibody according to any one of embodiments 1-4, wherein the heavy chain comprises:

a CDR1 sequence of amino acids 31-35 (GYPMN) of SEQ ID NO: 9, a CDR2 sequence of amino acids 50-66 (LINPYNGDT-TFNQKFKG) of SEQ ID NO: 9 and a CDR3 sequence of amino acids 99-106 (GTYEYVDY) of SEQ ID NO: 9;

and wherein the light chain comprises:

a CDR1 sequence of amino acids 24-33 (SASSSVFYMH) of SEQ ID NO: 11, a CDR2 sequence of amino acids 49-55 (DTSILSS) of SEQ ID NO: 11 and a CDR3 sequence of amino acids 88-96 (QQWSSYPLT) of SEQ ID NO: 11.

Embodiment 35: The antibody according to any one of embodiments 1-4, wherein the heavy chain comprises:

a CDR1 sequence of amino acids 31-35 (TYWIH) of SEQ ID NO: 13, a CDR2 sequence of amino acids 50-66 (AIDPGNS-DATYSQKFKD) of SEQ ID NO: 13 and a CDR3 sequence of amino acids 99-111 (EVYYGYDGDYFDY) of SEQ ID NO: 13;

and wherein the light chain comprises:

a CDR1 sequence of amino acids 24-38 (RASESVSVH-GTHLMH) of SEQ ID NO: 15, a CDR2 sequence of amino acids 54-60 (AASKLES) of SEQ ID NO: 15 and a CDR3 sequence of amino acids 93-101 (QQSIGDPWT) of SEQ ID NO: 15.

Embodiment 36: The antibody according to any one of embodiments 1-4, wherein the heavy chain of said antibody comprises SEQ ID NO: 5.

Embodiment 37: The antibody according to any one of embodiments 1-4 and 36, wherein the light chain of said antibody comprises SEQ ID NO: 7.

Embodiment 38: The antibody according to any one of embodiments 1-4, wherein the heavy chain of said antibody comprises SEQ ID NO: 9.

Embodiment 39: The antibody according to any one of embodiments 1-4 and 38, wherein the light chain of said antibody comprises SEQ ID NO: 11.

Embodiment 40: The antibody according to any one of embodiments 1-4, wherein the heavy chain of said antibody comprises SEQ ID NO: 13.

Embodiment 41: The antibody according to any one of embodiments 1-4 and 40, wherein the light chain of said antibody comprises SEQ ID NO: 15.

Embodiment 42: The antibody according to any one of embodiments 1-4, wherein said antibody comprises SEQ ID NO: 5 and SEQ ID NO: 7.

Embodiment 43: The antibody according to any one of embodiments 1-4, wherein said antibody comprises SEQ ID NO: 9 and SEQ ID NO: 11.

Embodiment 44: The antibody according to any one of embodiments 1-4, wherein said antibody comprises SEQ ID NO: 13 and SEQ ID NO: 15.

Embodiment 45: The antibody according to any one of the embodiments 1-44, which is a humanized antibody.

Embodiment 46: The antibody according to any one of the embodiments 1-45, wherein the isotype of said antibody is IgG.

Embodiment 47: The antibody according to embodiment 46, wherein said isotype is IgG1, IgG2 or IgG4.

Embodiment 48: The antibody according to embodiment 47, wherein the isotype of said antibody is IgG4.

Embodiment 49: The antibody, according to any one of embodiments 1-48, wherein the $K_D$ of said antibody is less than 4.0 nM, such as less than 3.0 nM, such as less than 2.0 nM, such as less than 1.0 nM, such as less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.02 nM, such as less than 0.01 nM.

Embodiment 50: The antibody according to any one of embodiments 1-49, which is not capable of binding truncated TFPI (1-185).

Embodiment 51: The antibody according to any one of embodiments 1-49, which is not capable of binding truncated TFPI (1-239).

Embodiment 52: The antibody according to any one of embodiments 1-51, which is not capable of binding the K1 or the K2 domain of TFPI.

Embodiment 53: The antibody according to any one of embodiments 1-52, which is not capable of binding GPI-anchored TFPI and/or lipoprotein bound TFPI.

Embodiment 54: The antibody according to any one of embodiments 1-53, which is capable of neutralizing TFPI inhibition of TF/FVIIa/FXa in the presence of phospholipid.

Embodiment 55: The antibody according to any one of embodiments 1-54, which is capable of binding the C-terminal of TFPI such that the percentage of free TFPI in a subject is reduced to less than 50%, such as less than 40%, such as less than 30%, such as less than 20%, such as less than 10%.

Embodiment 55a: The antibody according to any one of embodiments 1-55, which is capable of competing with MuTFPI4F110 for binding to TFPI.

Embodiment 55b: The antibody according to any one of embodiments 1-55, which is not capable of competing with MuTFPI4F110 for binding to TFPI.

Embodiment 56: The antibody according to any one of embodiments 1-55a, which reduces in vivo clotting time without significantly reducing the platelet count.

Embodiment 57: The antibody, according to embodiment 56, wherein said platelet count is not reduced to approximately 80%, such as approximately 75%, such as approximately 70%, such as approximately 65%, such as approximately 60%, such as approximately 55%, such as approximately 50%, such as approximately 45%, such as approximately 40%, such as approximately 35%, such as approximately 30%, such as approximately 25% of the original platelet count.

Embodiment 58: The antibody according to any one of embodiments 1-57, which reduces in vivo clotting time without causing transient thrombocytopaenia.

Embodiment 59: A pharmaceutical formulation comprising the antibody according to any one of embodiments 1-58.

Embodiment 59a: A pharmaceutical formulation comprising the antibody according to any one of embodiments 1-58 and a Factor VIIa, Factor VIII or Factor IX polypeptide.

Embodiment 60: The pharmaceutical formulation according to embodiment 59, which is suitable for parenteral use.

Embodiment 61: The pharmaceutical formulation according to embodiment 60, which is suitable for intravenous use.

Embodiment 62: The pharmaceutical formulation according to embodiment 60, which is suitable for subcutaneous use.

Embodiment 63: The antibody according to any one of embodiments 1-58, or the pharmaceutical formulation according to any one of embodiments 58-62, for the treatment of a subject with a coagulopathy.

Embodiment 64: The antibody according to any one of embodiments 1-58, or the pharmaceutical formulation according to any one of embodiments 58-62, for the treatment of any congenital, acquired and/or iatrogenic coagulopathy, such as may be selected from the group consisting of haemophilia A, with or without inhibitors, and haemophilia B, with or without inhibitors.

Embodiment 64a: The antibody according to any one of claims 1-9 and second coagulation agent, selected from the list consisting of a FVIIa polypeptide, a FVIII polypeptide or a FIX polypeptide, for the treatment of a subject with a coagulopathy.

Embodiment 64b: The antibody according to any one of embodiments 1-58 and a FVIII polypeptide for the treatment of haemophilia A.

Embodiment 64c: The antibody according to any one of embodiments 1-58 and a FIX polypeptide for the treatment of haemophilia B.

Embodiment 64d: The antibody according to any one of embodiments 1-58 and a FVIIa polypeptide for the treatment of haemophilia A or B with inhibitors.

Embodiment 65: A method of treating a subject with a coagulopathy, comprising administering to said subject the antibody according to any one of embodiments 1-58.

Embodiment 65a: A method of treating a subject with haemophilia A comprising administering to said subject the antibody according to any one of embodiments 1-58 and a FVIII polypeptide.

Embodiment 65b: A method of treating a subject with haemophilia B comprising administering to said subject the antibody according to any one of embodiments 1-58 and a FIX polypeptide.

Embodiment 65c: A method of treating a subject with FVII deficiency comprising administering to said subject the antibody according to any one of embodiments 1-58 and a FVII polypeptide.

Embodiment 65d: A method of treating a subject with haemophilia A with inhibitors, comprising administering to said subject the antibody according to any one of embodiments 1-58 and a FVII polypeptide.

Embodiment 65e: A method of treating a subject with haemophilia B with inhibitors, comprising administering to said subject the antibody according to any one of embodiments 1-58 and a FVII polypeptide.

Embodiment 66: The method according to embodiment 61, wherein said coagulopathy is any congenital, acquired and/or iatrogenic coagulopathy, such as may be selected from the group consisting of haemophilia A, with or without inhibitors, and haemophilia B, with or without inhibitors.

Embodiment 67: A polynucleotide that encodes the antibody according to any one of embodiments 1-58.

Embodiment 68: A polynucleotide according to embodiment 67, which comprises at least one sequence selected from the group consisting of SEQ ID NOs: 4, 6, 8, 10, 12 and 14.

Embodiment 69: A eukaryotic cell which comprises the polynucleotide according to any one of embodiments 67-69.

Embodiment 70: A eukaryotic cell which expresses the antibody, or fragment thereof, according to any one of embodiments 1-58.

Embodiment 71: The eukaryotic cell according to embodiment 70, which is a mammalian cell.

Embodiment 72: The mammalian cell according to embodiment 71, which is selected from the group consisting of HEK293, CHO, BHK, NSO and human retina cells.

The present invention is further illustrated by the following examples which should not be construed as further limiting. The contents of all figures and all references, patents and published patent applications cited throughout this application are expressly incorporated herein by reference.

EXAMPLES

Example 1

Immunisation and Fusion

Mice were immunized with full length TFPI (SEQ ID NO: 1).

RBF mice were used for immunizations and production of mouse monoclonal antibodies. Injections were made subcutaneously in the back of the mice. 20 µg TFPI was mixed with complete Freund's adjuvant for the first injection. In the subsequent immunizations, incomplete Freund's adjuvant was used with same concentration of the antigen. Ten days after the last immunization, eye-blood from mice was screened, using ELISA, for TFPI specific antibodies. Mice with positive serum titres were boosted with 10 µg of TFPI by intravenous injection, and sacrificed after three days. The spleens were removed aseptically and dispersed to a single cell suspension. Fusion of spleen cells and myeloma cells was done by the PEG-method or by electrofusion.

Screening Procedure
  Screening for binding to full length TFPI and no binding to TFPI(1-161)
  Cellular assays with endothelial cell lines or TF & TFPI transfected cells
  TFPI neutralizing activity in plasma (dilute prothrombin time)
  Clot dynamics measured in human plasma (Endogenous thrombin potential; ETP) and in human whole blood (thrombelastography; TEG)
  Identification of the specific inhibitory epitopes on full length soluble TFPI involved in binding of the monoclonal antibodies with the above characteristics Purification of mAbs
Monoclonal antibodies were purified by means of protein A affinity chromatography.

Example 2

Cloning and Sequencing of Mouse Anti-TFPI K3/C-Terminal Specific mAbs

This example describes cloning and sequencing of the murine heavy chain and light chain sequences of anti-TFPI antibodies MuTFPI4F110, MuTFPI22F66 and MuTFPI22F71.

Total RNA was extracted from hybridoma cells using the RNeasy-Mini Kit from Qiagen and used as template for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Start polymerase (Finnzymes) and the universal primer mix (UPM) included in the SMART™ RACE kit as forward primer. The sequence of the reverse primer used for HC (VH domain) amplification is given in SEQ ID NO: 16. The sequence of the reverse primer used for MuTFPI22F66 and MuTFPI22F71 LC (VL domain) amplification is given in SEQ ID NO: 17. The sequence of the reverse primer used for MuTFPI4F110 LC amplification is given in SEQ ID NO: 18.

PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 E. coli (Invitrogen). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at MWG Biotech, Martinsried Germany using M13uni(−21)/M13rev(−29) sequencing primers. Sequences were analyzed and annotated using the VectorNTI program. All kits and reagents were used according to the manufacturer's instructions.

A single unique murine kappa type LC and a single unique murine HC, subclass IgG1 was identified for each of the hybridomas: MuTFPI4F110, MuTFPI22F66 and MuTFPI22F71. Nucleic acid and amino acid sequences are as shown in the sequence listing; leader peptide sequences are not included.

Example 3

Dilute Prothrombin Time (dPT)

A dilute prothrombin (PT) analysis with human plasma in combination with diluted human thromboplastin. Clot time in the plasma was measured upon addition of increasing protein A purified TFPI monoclonal antibody concentrations to look for dose dependent reduction of clotting time with the mAbs of interest.

120 µl citrate-stabilized FVIII-depleted plasma (Helena) was mixed with 5 µl MuTFPI4F110 at various final concentrations (0.0-1.0 nM) and incubated for 15 min at room temperature. Clotting was measured by ACL300 analysis at 37° C. Coagulation was initiated by mixing 75 µl plasma with 75 µl reagent containing 0.02 M $CaCl_2$ and 1:3,750; 1:7,500; or 1:15,000 dilution of lipidated tissue factor (TF) (Innovin®) in 20 mM Hepes, 150 mM NaCl, pH 7.4. As shown in FIG. 1, MuTFPI4F110 shortened the clotting time in a concentration dependent manner at all three TF concentrations.

Only a fraction of TFPI present in plasma contains an intact C-terminal. This data suggests that binding of an antibody to this full length TFPI fraction efficiently promotes TF-induced clotting in FVIII-depleted plasma.

Example 4

Endogenous Thrombin Formation

Thrombin activity was assessed continuously following the conversion of the fluorogenic substrate Z-Gly-Gly-Arg-AMC.HCl (I-1140), from Bachem (Bubendorf, Switzerland). Fluorescence was measured in a microtiterplate Fluorskan Ascent fluorometer (Thermo Labsystems, Helsinki, Finland) with excitation and emission wavelengths set at 368 and 460 nm, respectively. A calibrator was used to allow calculation of the amount of thrombin formed and correction of the obtained relative fluorescence units for inner-filter effects and fluorogenic substrate consumption. In addition, the contribution to substrate conversion by thrombin-α2-macroglobulin complexes was subtracted (9). These corrections were performed automatically by means of the calibrated automated thrombogram (CAT) computer software provided by Synapse BV (Maastricht, the Netherlands). Finally, the first derivative of the data was taken that yielded the thrombin generation curve, allowing calculation of the total area under the curve, the endogenous thrombin potential (ETP).

Figure 2:
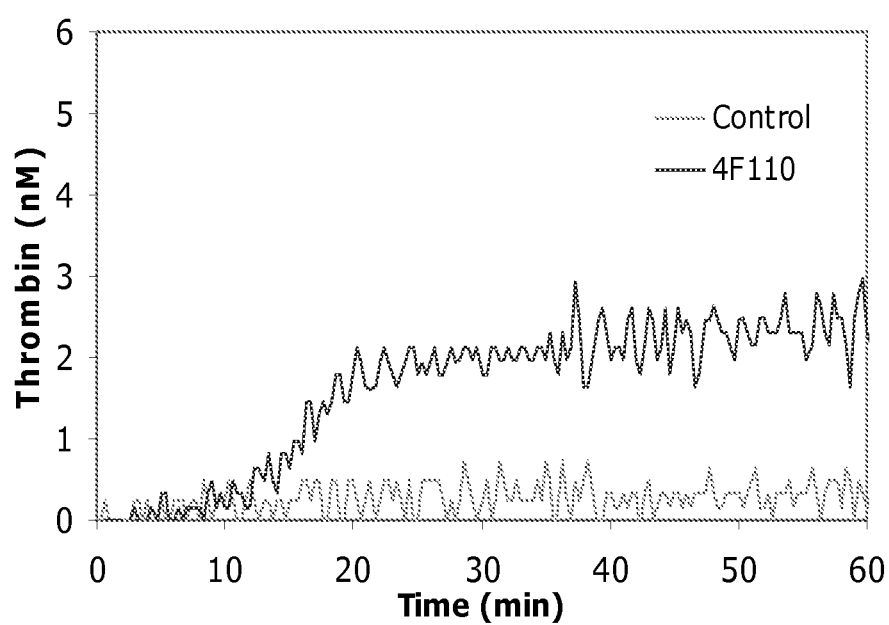
FIG. 2 shows the effect of 4F110 anti-TFPI on TF-induced thrombin generation in FVIII-depleted plasma. Clotting was initiated by calcification and addition of Innovin® (TF source) to citrated FVIII-depleted plasma supplemented with 10 μM PS/PC in the absence and presence of 10 nM 4F110.

The effect of MuTFPI4F110 on thrombin generation in FVIII-depleted plasma supplemented with 10 µM PS/PC is studied in FIG. 2. Triggering of coagulation by re-calcification and addition of Innovin® to a final dilution of 1/50,000 did not induce a measurable thrombin generation in the absence of anti-TFPI. In contrast, thrombin generation occurred in the presence of 10 nM MuTFPI4F110. After an initial increase the thrombin concentration reached a steady-state level of about 2 nM.

Figure 3:
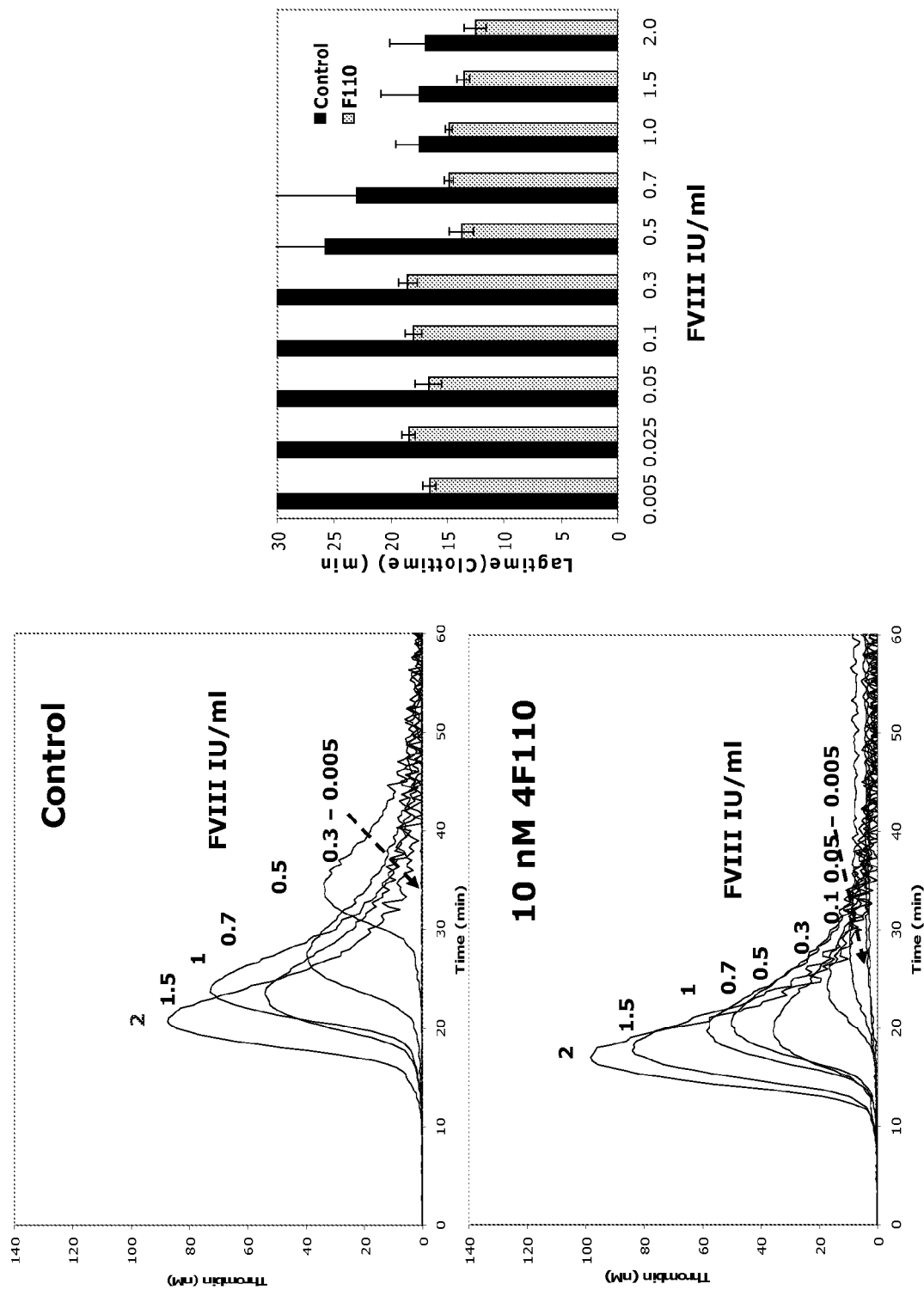
FIG. 3 shows the effect of 4F110 anti-TFPI on TF-induced thrombin generation in FVIII-depleted plasma replenished with various levels of rFVIII. Clotting was initiated by calcification and addition of Innovin® (TF source) to citrated FVIII-depleted plasma supplemented with 10 μM PS/PC in the absence and presence of 10 nM 4F110. Bars show the corresponding lag times calculated based on a thrombin threshold level of 1 nM (means±SD, n=x).
Figure 4:
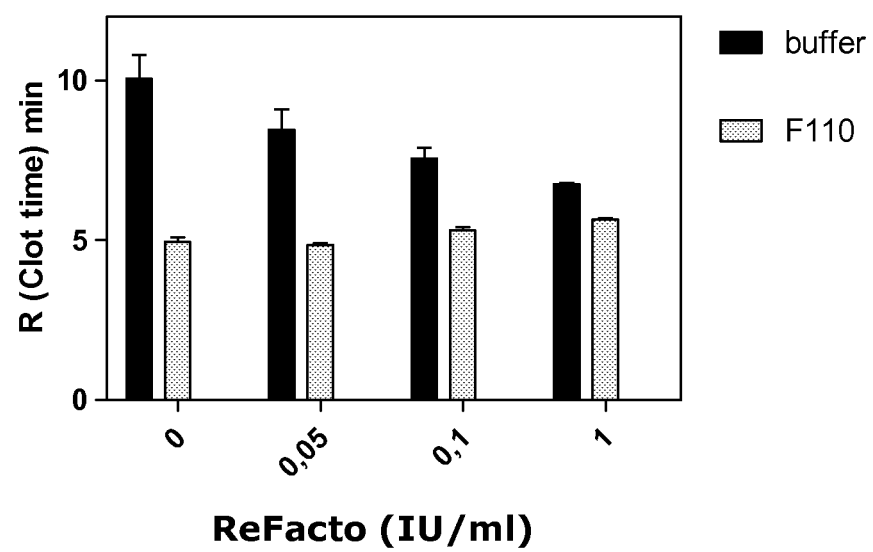
FIG. 4 shows the effect of 4F110 anti-TFPI and rFVIII on TF-induced clot formation in FVIII-depleted plasma supplemented with 150,000 platelets/μl measured by thromboelastography (TEG) analysis. A. TEG curves show the effect of adding 0.005, 0.05 and 1.0 U/ml rFVIII to FVIII-depleted plasma in the absence of anti-TFPI. B. TEG curves show the effect of adding 0.005, 0.05 and 1.0 U/ml rFVIII to FVIII depleted plasma in the presence of 10 nM 4F110 anti-TFPI C. R values (clot times) for the curves without AB shown in A (open bars) and with AB shown in B (closed bars). D. K (speed of clot kinetics) values for the curves without AB shown in A (open bars) and with AB shown in B (closed bars). E. Angle values for the curves without AB shown in A (open bars) and with AB shown in B (closed bars). F. MA (maximal amplitude) values for the curves without AB shown in A (open bars) and with AB shown in B (closed bars).
Figure 4:
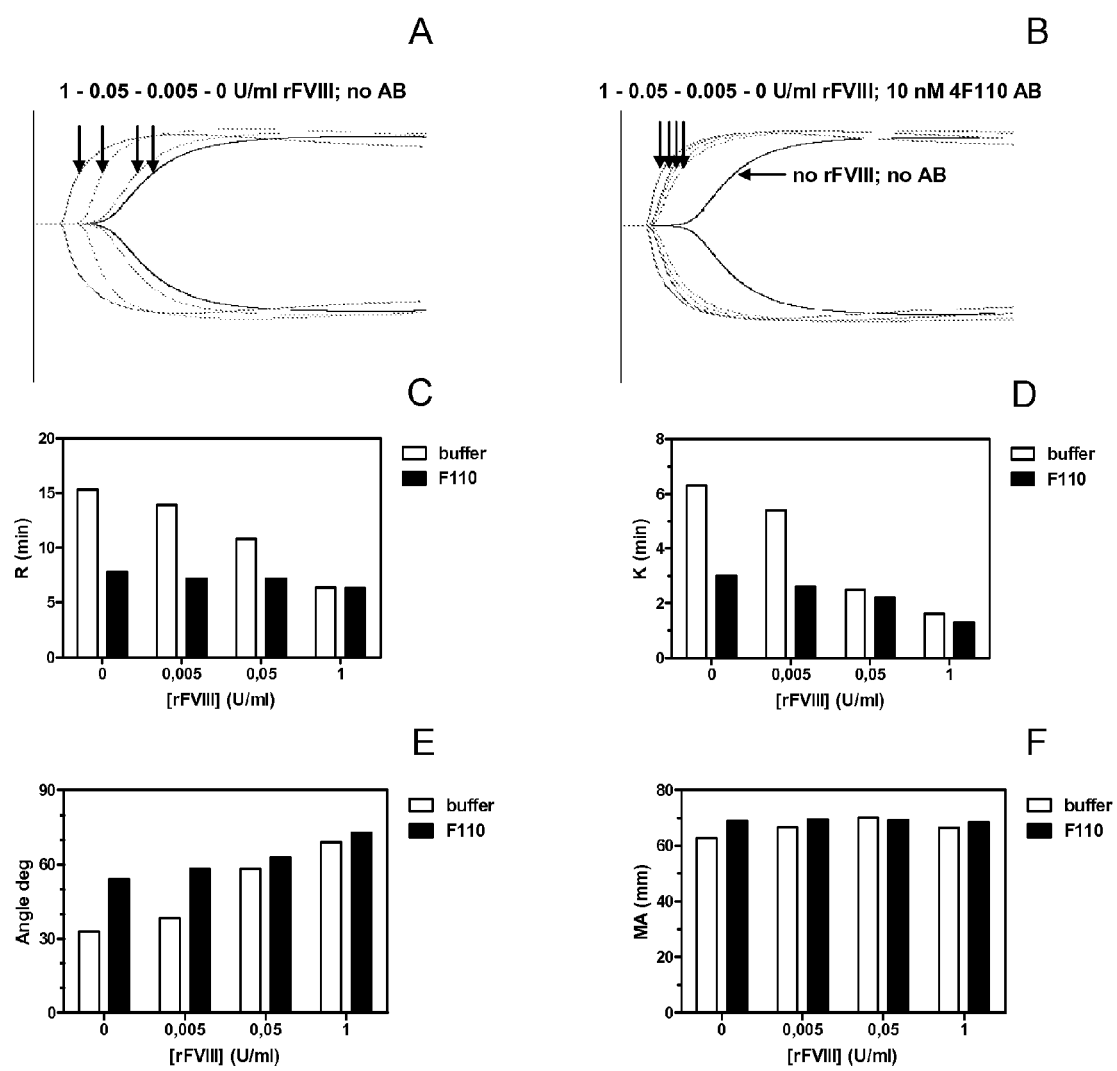

MuTFPI4F110 was studied in the presence of sub-normal levels of FVIII, typical for severe and moderate hemophilia A, to see if it is capable of improving or normalising the thrombin generation. The results in FIG. 3 show the effect on TF-induced thrombin generation of replenishing FVIII-depleted plasma with 0-2 IU/ml rFVIII (REFacto®) in absence and presence of 10 nM MuTFPI4F110. Thrombin generation was below the detection level in the absence of added rFVIII and was measurable only when rFVIII was added to a level higher than ~0.3 IU/ml rFVIII. Supplementation with higher levels of rFVIII resulted in a dose-dependent increase in the thrombin activity peak and shortened the lag time to thrombin generation. Thrombin generation experiments in the presence of 10 nM MuTFPI4F110 showed that neutralization of TFPI in FVIII-depleted plasma resulted in enhancement of thrombin generation, as illustrated in FIG. 2, at a higher resolution. After a lag time of about 13 min the thrombin concentration increased and reached a steady-state level of about 2 nM. Addition of rFVIII to levels higher than about 0.05 IU/ml changed this pattern and induced an additional transient thrombin peak on top of the basal steady-state level induced by MuTFPI4F110 alone. The results showed that MuTFPI4F110 directed towards the C-terminal of TFPI alone promotes initiation of coagulation, and, in combination with sub-optimal levels of FVIII, it also enhances the generation of a thrombin burst.

Example 5

Thrombelastography (TEG) Measurements

Citrate-stabilized FVIII-depleted plasma (Helena) was supplemented with (final concentrations): 0.12 pM TF (Innovin®, 1:50,000), 150,000 washed platelets/µl and various concentrations (0.0; 0.005; 0,05; 0,01 and 1.0 U/ml) of recombinant FVIII (ReFacto®). Clotting in the absence or presence of 10 nM MuTFPI4F110 was initiated when 320 µl of this premix was transferred to a thrombelastograph cup containing 20 µl 0.2 M CaCl$_2$. The TEG trace was followed continuously for up to 120 min (5000 series TEG analyzer, Haemoscope Corporation, Niles, Ill., USA). The following TEG variables were recorded: R time (clotting time i.e. the time from initiation of coagulation until an amplitude of 2 mm was obtained), α-angle (clot development measured as the angle between the R value and the inflection point of the TEG trace), K (speed of clot kinetics to reach a certain level of clot strength, amplitude=20 mm), and MA (maximal amplitude of the TEG trace reflecting the maximal mechanical strength of the clot).

The results showed that MuTFPI4F110 enhanced the TF-induced clot formation i.e. shortened the clotting time (R value) and enhanced the rate of clot development (angle value) both in the absence of rFVIII and at low concentrations of rFVIII, corresponding to severe and moderate hemophilia.

Example 6

FACS Analysis

The TFPI-positive human endothelial-like immortalised cell line EAHy926WT (derived from umbilical vein endothelial cells) were used as a positive control for binding of membrane bound TFPI. The aerolysin-resistant EAHy926AR cells do not express TFPI on their surface and were used as a negative control.

Staining with anti TFPI antibodies and the corresponding isotype control antibody hzATNP were done as follows: Washed cell-line preparations (50000 cells pr well) were added to 96 well plates (Greiner, cat no. 65021) together with 50 µl of diluted TFPI antibody or isotype control in titration giving final concentrations 5 µg/ml. Cell preparations were then incubated at 4 degrees Celsius for 1 hour. After incubation and wash (PBS buffer with 5% Fetal calf serum, centrifuge for 5 minutes at 200 g) the secondary RPE-labelled anti-human antibody (diluted in PBS buffer 1:200) was added and incubated for another 1 hour at 4 degrees of Celsius. Finally, cells were washed and fixed by paraformaldehyde (1% weight in volume (w/v) paraformaldehyde) and analysed in the flow cytometer within 36 hours.

Figure 5:
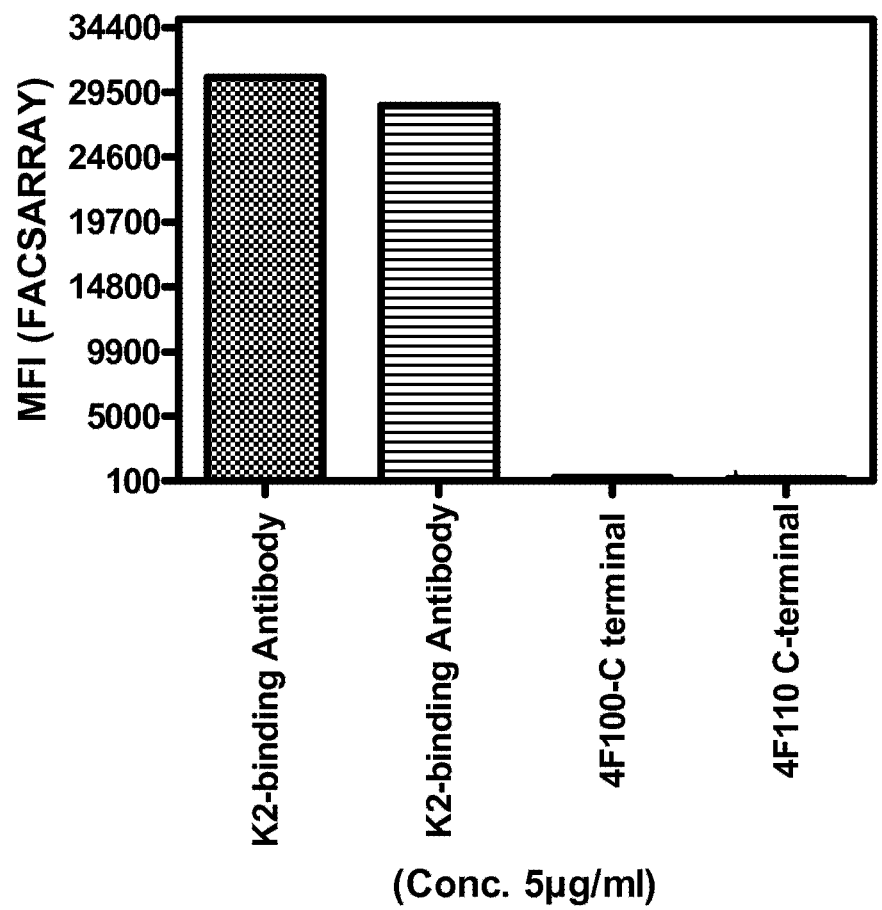
FIG. 5 shows the fluorescence-activated cell sorter (FACS) analysis of a TFPI-expressing cell line. As also illustrated in FIG. 6, the two C-terminal monoclonal antibodies were not able to bind to TFPI on a cellular surface.
Figure 6:
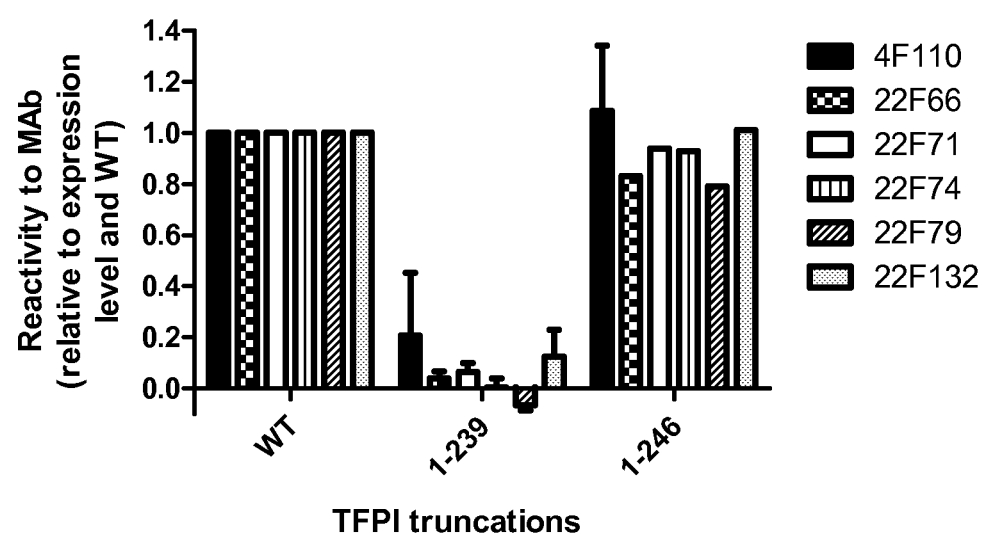
FIG. 6 shows that the C-terminal TFPI antibodies named 4F110, 22F66, 22F71, 22F74, 22F79 and 22F132 do not bind or bind very poorly to truncated TFPI(1-239) (middle five bars).

In FIG. 5, the binding of C-terminal specific anti TFPI antibodies (4F100 and 4F110) and the isotype control antibody hzATNP (0.5 µg/ml) to EAHy926WT and EAHy926AR is shown.

It is here clear that anti-TFPI antibodies directed against the C-terminal of TFPI do not bind TFPI anchored via GPI expressed by endothelial cell line EAHy926WT, whereas antibodies to Kunitz 2 bind selectively to the EAHy926WT and not to the aerolysin resistant TFPI negative cell line EAHy926AR.

Example 7

ELISA

The effect of truncating the C-terminal tail of TFPI on TFPI's binding affinity to MuTFPI22F66, MuTFPI22F71, MuTFPI22F74, MuTFPI22F79 and MuTFPI22F132 was analyzed by means of ELISA, or real-time binding analysis, using the ForteBio platform. The TFPI variants, which were either wild type (wt) TFPI (SEQ ID NO: 1) or truncated TFPI mutants encompassing amino acids 1-239 (SEQ ID NO: 2), 1-240 (SEQ ID NO: 22), 1-241 (SEQ ID NO: 23), 1-242 (SEQ ID NO: 24), 1-243 (SEQ ID NO: 25), 1-244 (SEQ ID NO: 26) or 1-245 (SEQ ID NO: 3), were expressed in HEK293-F cells. The ELISAs, or the real-time binding analyses, were carried out using the conditioned medium from the cell cultures.

The concentrations of wt TFPI and truncated TFPI mutants in the conditioned medium were estimated by means of an ELISA that binds TFPI K1-K2 (Goat anti-TFPI, in-house) and K2 (MAb4F36, in-house). The binding to these antibodies is not affected by the truncations. Alternatively, biotin-labelled MAb4F36 was captured on streptavidin coated BioSensor tips (ForteBio) and used for concentration estimations.

In the ELISA setting, the effect of the mutations on TFPI's ability to bind to MuTFPI22F66, MuTFPI22F71, MuTFPI22F74, MuTFPI22F79 or MuTFPI22F132 was analyzed using each of the listed MAbs as capturing antibody and using MAb4F36 for detection. Direct binding of TFPI variants to biotin-labelled MuTFPI22F66, MuTFPI22F71, MuTFPI22F74, MuTFPI22F79, and MuTFPI22F132, captured on streptavidin coated BioSensor tips (ForteBio), was measured using the ForteBio platform.

Figure 7:
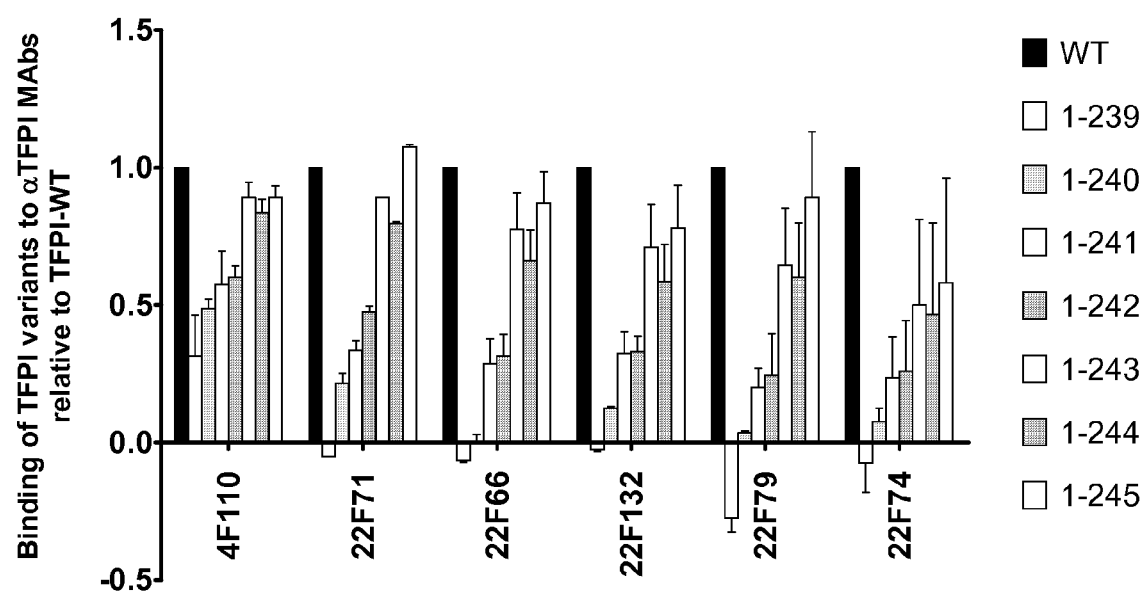
FIG. 7 shows that six TFPI antibodies (4F110, 22F66, 22F71, 22F132, 22F79, 22F74) bind to different truncated forms of TFPI, listed at the right. Binding is relative to the binding to wild type (wt) TFPI (1.0).
Figure 8:
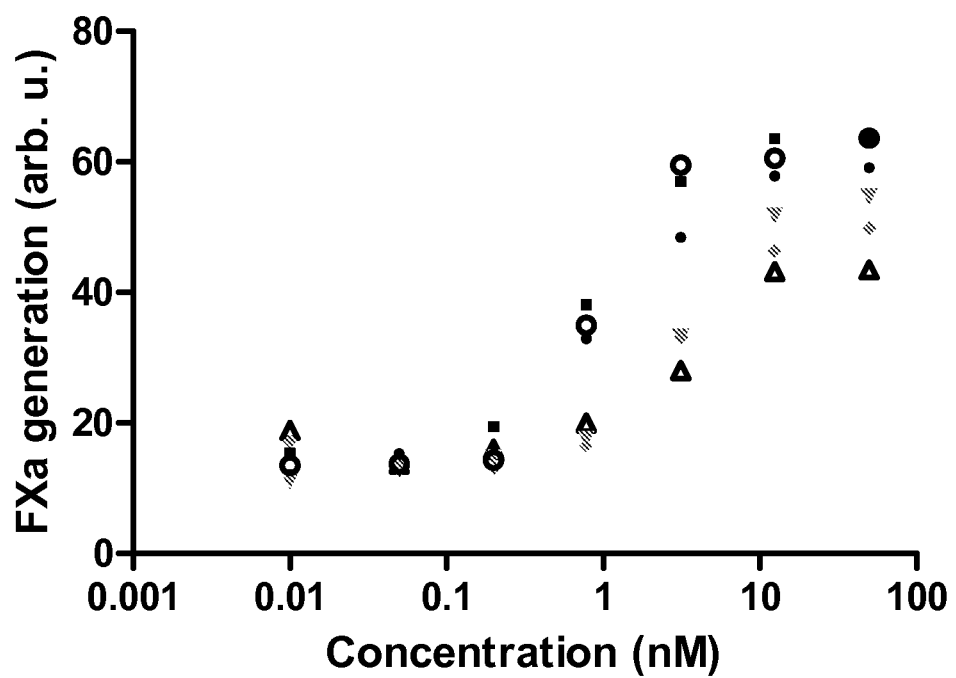
FIG. 8 shows the neutralization of TFPI inhibition of FVIIa/TF/FXa activity in the presence of phospholipid (PS/PC) vesicles. Open circle: 4F110; filled circle 22F66; square: 22F71; grey triangle: 22F79; open triangle: 22F74; grey rhombus: 22F132.
Figure 9:
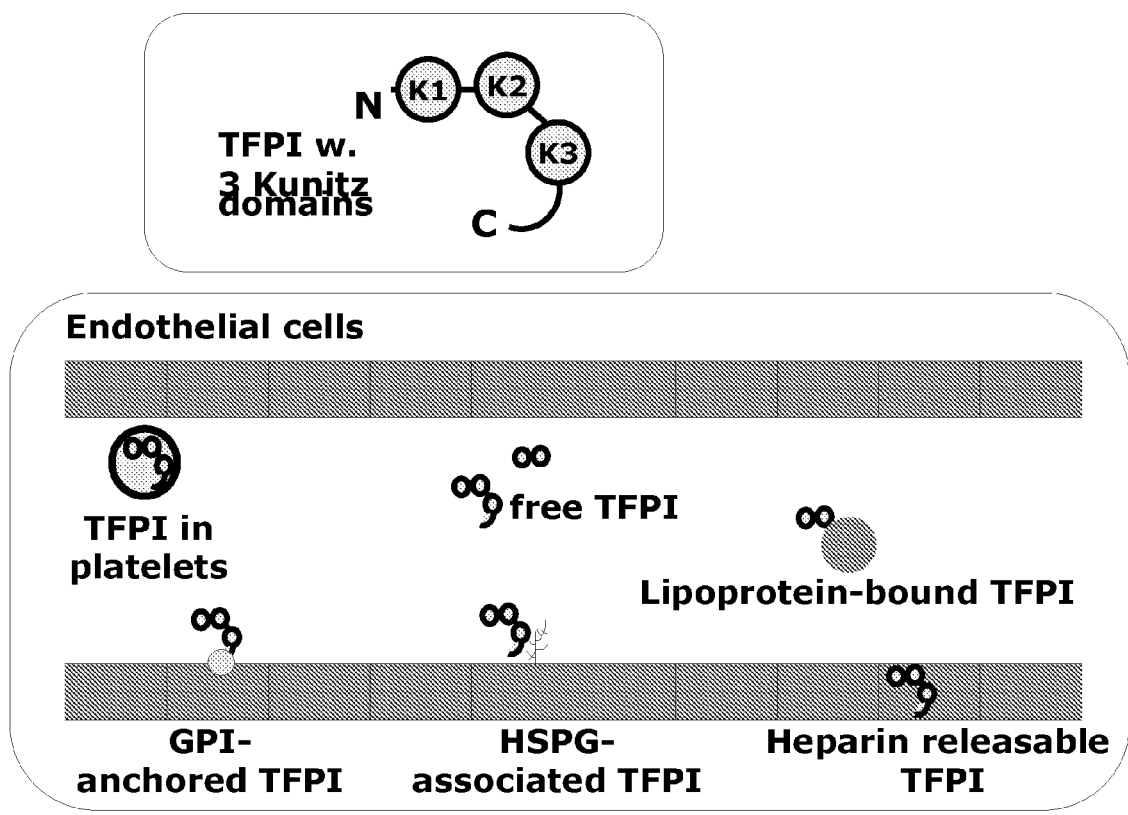
FIG. 9 is a cartoon of the structure of TFPI and the various pools of TFPI.

FIG. 7 reflects the effect of the truncations calculated, relative to the expression level and relative to wt. It was demonstrated that mAb 4F110 binding to the three truncated forms 1-243, 1-244 and 1-245 was not affected, compared to their binding to full length TFPI, whereas binding of mAb 22F74 to all of the truncated TFPI forms was strongly reduced. The rest of the tested antibodies lay within this range.

Example 8

Neutralizing TFPI Inhibition of FVIIa/TF/FXa Activity in the Presence of PS/PC Vesicles Materials used were BSA buffer (50 mM Hepes; 0.1 M NaCl, 5 mM $CaCl_2$, 0.1 mg/ml BSA, pH 7.4) EDTA: 50 mM and the reagents listed in the tables below.

| Sample ID mAB | Batch | conc mg/ml | conc nM | Working solution nM | Dilution factor |
|---|---|---|---|---|---|
| 1 TFPI-22F66 | BA002-2 | 2.2 | 14667 | 400 | 36.7 |
| 2 TFPI-22F71 | BA002-3 | 0.5 | 3333 | 400 | 8.3 |
| 3 TFPI-22F74 | BA002-5 | 0.6 | 4000 | 400 | 10 |
| 4 TFPI-22F79 | BA002-6 | 4.8 | 32000 | 400 | 80 |
| 5 TFPI-22F132 | BA002-7 | 5.2 | 34667 | 400 | 86.7 |
| 6 TFPI-4F110 | OP001 | 3.5 | 23333 | 400 | 58.3 |

| Reagent | Batch - lot no. | Conc | Final conc in well |
|---|---|---|---|
| EDTA | MERCK 8418 | 0.5M | |
| mAb | | | nM |
| | | | 50 |
| | | | 12.5 |
| | | | 3.13 |
| | | | 0.78 |
| | | | 0.2 |
| | | | 0.05 |
| | | | 0.01 |
| | | | 0 |
| FVIIa | LASa 13200-008 frozen in aliquots storage −80° C. | 27 μM | 10 pM |
| vesicles | HTI Phospholipids vesicles cat#PCPS-02 #W1115-75% PC - 25% PS (0.02% azid added) | 2.0 mM | 12.5 μM |
| S-2765 | Chromogenix 82 1413 39 lot#N0574120 2010-50 | 35 mM | 0.5 mM |
| FX | Enzyme Research HXF 3064 A2L dissolved in 50% Glycerol 08 Dec. 2009 frozen in aliquots storage −80° C. | 34 μM | 160 nM |
| TFPI Fl. | 0172-0000-0001-6A aliqouts storage −20° C. | 21.9 μM | 1 nM |
| TF (Innovin) | Dade Behring#B4212-50# vial diss. in 10 ml H2O 08 Dec. 2009, frozen in aliquots storage −20° C. | 6 nM | 10 pM |

All of the components, in final concentrations as indicated in the table above, were added together. 25 μl FX and 25 μl TFPI mAb were added in varying concentrations to 25 μl human TFPI, 25 μl FVIIa-TF (innovin) and PS/PC vesicles in microtiter wells. Mixtures were incubated for 15 min at room temperature. 50 μl EDTA was added, followed by 50 μl S-2765. Plates were mixed and read for 15 min at 405 nm in Spectramax. 100% activity was the activity of FVIIa/TF/FX obtained with no TFPI present.

The six C-terminal TFPI mAbs listed in the table above were capable of neutralising TFPI inhibition of the complex FVIIa/TF/FX in the presence of PS/PC vesicles. The antibodies also neutralised TFPI in the absence of PS/PC.

Example 9

Binding Interaction Analysis

Binding interaction analysis was obtained by Surface Plasmon Resonance in a Biacore 3000. Capture of the relevant monoclonal antibody at a fixed concentration was obtained with immobilised mouse anti-IgG. Different concentrations of TFPI were tested. Determination of binding constants ($k_{on}$, $k_{off}$, $K_D$) was obtained assuming a 1:1 interaction of TFPI and the antibody of interest.

| | TFPI binding constant nM | | | |
|---|---|---|---|---|
| mAB ID | Human TFPI | Human $TFPI_{161}$ | Rabbit TFPI | Rabbit $TFPI_{161}$ |
| MuTFPI22F66 | 0.6 | — | 3.76 | — |
| MuTFPI22F71 | 0.8 | — | 0.18 | — |
| MuTFPI22F74 | nd | — | 2.73 | — |
| MuTFPI22F132 | nd | — | 0.1 | — |
| MuTFPI4F110 | 0.002 | — | — | — |

Competition of the different mAbs for binding to TFPI when bound to mAb 4F110 was obtained by immobilisation of mAb 4F110 at a CM5 chip followed by binding of 50 nM TFPI followed by varying concentrations the mAbs (22F66, 22F71, 22F74, 22F79, 22F132, 22F158, 22F174, 4F110) to be tested for competition. Results are shown in the table below. Regeneration of the chip was obtained by 10 mM Glycine, pH 1.7.

| mAb ID | Competition with mAB 4F110 for binding to TFPI |
|---|---|
| TFPI-22F66 | YES |
| TFPI-22F71 | YES |
| TFPI-22F74 | NO |
| TFPI-22F79 | NO |
| TFPI-22F132 | NO |
| TFPI-22F158 | YES |
| TFPI-22F174 | YES |
| TFPI-4F110 | YES |

The C-terminal mAbs fall into two groups with respect to competition with mAb 4F110. Antibodies in both groups display TFPI neutralizing activity.

Example 10

Epitope Determination by Means of Comparative Modelling

Epitope models were generated by means of the commercially available computer program, Modeller [N. Eswar, M. A. Marti-Renom, B. Webb, M. S. Madhusudhan, D. Eramian, M. Shen, U. Pieper, A. Sali. Comparative Protein Structure Modeling With MODELLER. Current Protocols in Bioinformatics, John Wiley & Sons, Inc., Supplement 15, 5.6.1-5.6.30, 2006] based on published x-ray crystallographic structures of TFPI1-2. For the TFPI1-3, residues with a relative accessibility larger than 40% were found to be: 186-187, 190, 192-208, 213, 215-220, 225-228, 230-234 and 236-237. For the C-terminal, residues 240-276 had a relative accessability that was larger than 40%.

Example 11

Factor VIIa Variant Activity Assay (In Vitro Hydrolysis Assay)

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a Spectra-Max™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

Ratio=($A_{405\,nm}$ Factor VIIa variant)/($A_{405\,nm}$ Factor VIIa wild-type).

Example 12

Factor VIIa Variant Activity Assay (In Vitro Proteolysis Assay)

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a Spectra-Max™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=($A_{405\,nm}$ Factor VIIa variant)/($A_{405\,nm}$ Factor VIIa wild-type).

Example 13

Factor VIII Activity Assay (Chromogenic Assay)

The FVIII activity (FVIII:C) of the rFVIII compound is evaluated in a chromogenic FVIII assay using Coatest SP reagents (Chromogenix) as follows: rFVIII samples and a FVIII standard (e.g. purified wild-type rFVIII calibrated against the 7th international FVIII standard from NIBSC) are diluted in Coatest assay buffer (50 mM Tris, 150 mM NaCl, 1% BSA, pH 7.3, with preservative). Fifty μl of samples, standards, and buffer negative control are added to 96-well microtiter plates (Nunc) in duplicates. The factor IXa/factor X reagent, the phospholipid reagent and $CaCl_2$ from the Coatest SP kit are mixed 5:1:3 (vol:vol:vol) and 75 μl of this added to the wells. After 15 min incubation at room temperature, 50 μl of the factor Xa substrate S-2765/thrombin inhibitor I-2581 mix is added and the reagents incubated for 10 minutes at room temperature before 25 μl 1 M citric acid, pH 3, is added. The absorbance at 415 nm is measured on a Spectramax microtiter plate reader (Molecular Devices) with absorbance at 620 nm used as reference wavelength. The value for the negative control is subtracted from all samples and a calibration curve prepared by linear regression of the absorbance values plotted vs. FVIII concentration. Specific activity is calculated by dividing the activity of the samples with the protein concentration determined by HPLC. The concentration of the sample is determined by integrating the area under the peak in the chromatogram corresponding to the light chain and compare with the area of the same peak in a parallel analysis of a wild-type unmodified rFVIII, where the concentration is determined by amino acid analyses.

Example 14

Factor VIII Activity Assay (One-Stage Clot Assay)

FVIII activity (FVIII:C) of the rFVIII compounds is further evaluated in a one-stage FVIII clot assay as follows: rFVIII samples and a FVIII standard (e.g. purified wild-type rFVIII calibrated against the 7th international FVIII standard from NIBSC) are diluted in HBS/BSA buffer (20 mM hepes, 150 mM NaCl, pH 7.4 with 1% BSA) to approximately 10 U/ml, followed by 10-fold dilution in FVIII-deficient plasma containing VWF (Dade Behring). Samples are subsequently diluted in HBS/BSA buffer. The APTT clot time is measured using an ACL300R or an ACL5000 instrument (Instrumentation Laboratory) using the single factor program. FVIII-deficient plasma with VWF (Dade Behring) is used as assay plasma and SynthASil, (HemosIL™, Instrumentation Laboratory) as aPTT reagent. In the clot instrument, the diluted sample or standard is mixed with FVIII-deficient plasma and aPTT reagents at 37° C. Calcium chloride is added and time until clot formation is determined by measuring turbidity. The FVIII:C in the sample is calculated based on a standard curve of the clot formation times of the dilutions of the FVIII standard.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A monoclonal antibody that specifically binds the C-terminal of TFPI,
wherein said C-terminal is amino acids 186-276 of TFPI (SEQ ID NO: 1), wherein said antibody comprises a heavy chain comprising a CDR1 sequence of amino acids 31 to 35 (SYYMY) of SEQ ID NO: 5; a CDR2 sequence of amino acids 50-66 (EINPSNGDTNLNEKFKS) of SEQ ID NO: 5; and a CDR3 sequence of amino acids 99-107 (WDRFDGFVY) of SEQ ID NO: 5; and a light chain comprising a CDR1 sequence of amino acids 24-34 (IISTNIDDDIN) of SEQ ID NO: 7; a CDR2 sequence of amino acids 50-56 (EGNTLRP) of SEQ ID NO: 7; and a CDR3 sequence of amino acids 89-97 (LQSDDLPYT) of SEQ ID NO: 7,
or said antibody comprises a heavy chain comprising a CDR1 sequence of amino acids 31-35 (GYPMN) of SEQ ID NO: 9; a CDR2 sequence of amino acids 50-66 (LINPYNGDTTFNQKFKG) of SEQ ID NO: 9; and a CDR3 sequence of amino acids 99-106 (GTYEYVDY) of SEQ ID NO: 9; and a light chain comprising: a CDR1 sequence of amino acids 24-33 (SASSSVFYMH) of SEQ ID NO: 11; a CDR2 sequence of amino acids 49-55 (DTSILSS) of SEQ ID NO: 11; and a CDR3 sequence of amino acids 88-96 (QQWSSYPLT) of SEQ ID NO: 11,
or said antibody comprises a heavy chain comprising a CDR1 sequence of amino acids 31-35 (TYWIH) of SEQ ID NO: 13; a CDR2 sequence of amino acids 50-66 (AIDPGNSDATYSQKFKD) of SEQ ID NO: 13; and a CDR3 sequence of amino acids 99-111 (EVYYGYDGDYFDY) of SEQ ID NO: 13; and a light chain comprising a CDR1 sequence of amino acids 24-38 (RASESVSVHGTHLMH) of SEQ ID NO: 15; a CDR2 sequence of amino acids 54-60 (AASKLES) of SEQ ID NO: 15; and a CDR3 sequence of amino acids 93-101 (QQSIGDPWT) of SEQ ID NO: 15.

2. The monoclonal antibody according to claim 1, wherein the heavy chain comprises:
a CDR1 sequence of amino acids 31 to 35 (SYYMY) of SEQ ID NO: 5;
a CDR2 sequence of amino acids 50-66 (EINPSNGDTNLNEKFKS) of SEQ ID NO: 5; and
a CDR3 sequence of amino acids 99-107 (WDRFDGFVY) of SEQ ID NO: 5; and the light chain comprises:
a CDR1 sequence of amino acids 24-34 (IISTNIDDDIN) of SEQ ID NO: 7;
a CDR2 sequence of amino acids 50-56 (EGNTLRP) of SEQ ID NO: 7; and
a CDR3 sequence of amino acids 89-97 (LQSDDLPYT) of SEQ ID NO: 7.

3. The monoclonal antibody according to claim 2, wherein said antibody comprises SEQ ID NO: 5 and SEQ ID NO: 7.

4. The monoclonal antibody according to claim 1, which is not capable of specifically binding truncated TFPI (1-185).

5. The monoclonal antibody according to claim 1, which neutralizes TFPI inhibition of TF/FVIIa/FXa in the presence of phospholipid.

6. A pharmaceutical formulation comprising the monoclonal antibody according to claim 1.

7. The monoclonal antibody according to claim 1, wherein the heavy chain comprises:
a CDR1 sequence of amino acids 31-35 (GYPMN) of SEQ ID NO: 9;
a CDR2 sequence of amino acids 50-66 (LINPYNGDTTFNQKFKG) of SEQ ID NO: 9; and
a CDR3 sequence of amino acids 99-106 (GTYEYVDY) of SEQ ID NO: 9; and the light chain comprises:
a CDR1 sequence of amino acids 24-33 (SASSSVFYMH) of SEQ ID NO: 11;
a CDR2 sequence of amino acids 49-55 (DTSILSS) of SEQ ID NO: 11; and
a CDR3 sequence of amino acids 88-96 (QQWSSYPLT) of SEQ ID NO: 11.

8. The monoclonal antibody according to claim 7, wherein said antibody comprises SEQ ID NO: 9 and SEQ ID NO: 11.

9. The monoclonal antibody according to claim 1, wherein the heavy chain comprises:
a CDR1 sequence of amino acids 31-35 (TYWIH) of SEQ ID NO: 13;
a CDR2 sequence of amino acids 50-66 (AIDPGNSDATYSQKFKD) of SEQ ID NO: 13; and
a CDR3 sequence of amino acids 99-111 (EVYYGYDGDYFDY) of SEQ ID NO: 13; and the light chain comprises:
a CDR1 sequence of amino acids 24-38 (RASESVSVHGTHLMH) of SEQ ID NO: 15;
a CDR2 sequence of amino acids 54-60 (AASKLES) of SEQ ID NO: 15; and
a CDR3 sequence of amino acids 93-101 (QQSIGDPWT) of SEQ ID NO: 15.

10. The monoclonal antibody according to claim 9, wherein said antibody comprises SEQ ID NO: 13 and SEQ ID NO: 15.

11. The monoclonal antibody according to claim 1, which neutralizes TFPI inhibition of TF/FVIIa/FXa.

12. A pharmaceutical formulation comprising the monoclonal antibody according to claim 2.

13. A method of treating a subject with a coagulopathy, comprising administering to said subject the monoclonal antibody according to claim 1.

14. The method of treating a subject with a coagulopathy of claim 13, wherein the coagulopathy is hemophilia A.

15. A method of treating a subject with a coagulopathy, comprising administering to said subject the monoclonal antibody according to claim 2.

16. The method of claim 15, wherein the coagulopathy is hemophilia A.

* * * * *

SEQUENCE LISTING

<160> NUMBER OF SEQ ID NOS: 26

<210> SEQ ID NO 1
<211> LENGTH: 276
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
            275

<210> SEQ ID NO 2
<211> LENGTH: 239
<212> TYPE: PRT
<213> ORGANISM: Artificial sequence
<220> FEATURE:
<223> OTHER INFORMATION: Truncated TFPI (1-239)

<400> SEQUENCE: 2

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

```
Gly Pro Cys Lys Ala Ile Met Lys Arg Phe Phe Asn Ile Phe Thr
            35                  40                  45

Arg Gln Cys Glu Glu Phe Ile Tyr Gly Gly Cys Glu Gly Asn Gln Asn
 50                  55                  60

Arg Phe Glu Ser Leu Glu Glu Cys Lys Lys Met Cys Thr Arg Asp Asn
 65                  70                  75                  80

Ala Asn Arg Ile Ile Lys Thr Thr Leu Gln Gln Glu Lys Pro Asp Phe
                 85                  90                  95

Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
                195                 200                 205

Ser Val Ile Gly Lys Cys Arg Pro Phe Lys Tyr Ser Gly Cys Gly Gly
        210                 215                 220

Asn Glu Asn Asn Phe Thr Ser Lys Gln Glu Cys Leu Arg Ala Cys
225                 230                 235

<210> SEQ ID NO 3
<211> LENGTH: 245
<212> TYPE: PRT
<213> ORGANISM: Artificial sequence
<220> FEATURE:
<223> OTHER INFORMATION: Truncated TFPI (1-245)

<400> SEQUENCE: 3

Asp Ser Glu Glu Asp Glu His Thr Ile Ile Thr Asp Thr Glu Leu
 1               5                  10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Asn Ile Phe Thr
            35                  40                  45

Arg Gln Cys Glu Glu Phe Ile Tyr Gly Gly Cys Glu Gly Asn Gln Asn
 50                  55                  60

Arg Phe Glu Ser Leu Glu Glu Cys Lys Lys Met Cys Thr Arg Asp Asn
 65                  70                  75                  80

Ala Asn Arg Ile Ile Lys Thr Thr Leu Gln Gln Glu Lys Pro Asp Phe
                 85                  90                  95

Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160
```

```
Thr Gln Leu Asn Ala Val Asn Ser Leu Thr Pro Gln Ser Thr Lys
            165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
210                 215                 220

Asn Glu Asn Asn Phe Thr Ser Lys Gln Glu Cys Leu Arg Ala Cys Lys
225                 230                 235                 240

Lys Gly Phe Ile Gln
            245

<210> SEQ ID NO 4
<211> LENGTH: 354
<212> TYPE: DNA
<213> ORGANISM: Mus musculus

<400> SEQUENCE: 4
caggtccaac tgcagcagtc tggggctgaa ctggtgaagc ctggggcttc agtgaagttg      60
tcctgcaagg cttctggcta caccttcatc agttactata tgtactgggt gaagcagagg     120
cctggacaag ccttgagtg gattggagag attaatccta gcaatggtga tactaacctc     180
aatgagaagt tcaagagcaa ggccacactg actgtagaca atcctccag cacagtatac      240 atgcaactca gcagcctgac atctgaggac tctgcggtct attactgtac aagatgggat     300
aggttcgacg gttttgttta ctggggccaa gggactctgg tcactgtctc tgca            354

<210> SEQ ID NO 5
<211> LENGTH: 118
<212> TYPE: PRT
<213> ORGANISM: Mus musculus

<400> SEQUENCE: 5

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Asp Thr Asn Leu Asn Glu Lys Phe
    50                  55                  60

Lys Ser Lys Ala Thr Leu Thr Val Asp Lys Ser Ser Ser Thr Val Tyr
65                  70                  75                  80

Met Gln Leu Ser Ser Leu Thr Ser Glu Asp Ser Ala Val Tyr Tyr Cys
            85                  90                  95

Thr Arg Trp Asp Arg Phe Asp Gly Phe Val Tyr Trp Gly Gln Gly Thr
        100                 105                 110

Leu Val Thr Val Ser Ala
    115

<210> SEQ ID NO 6
<211> LENGTH: 324
<212> TYPE: DNA
<213> ORGANISM: Mus musculus

<400> SEQUENCE: 6
```

```
gaaacaactg tgacccagtc tccagcatcc ctgtccatgg ctataggagg aaaagtcacc    60
atcagatgca taatcagcac taatattgat gatgatataa actggtacca gcagaagcca   120
ggggaacctc ctaagctcct tatttcagaa ggcaatactc ttcgtcctgg agtcccatcc   180
cgattctcca gcagtggcta tggtacagat tttgttttta caattgaaaa catgctctca   240
gaagatgttg cagattacta ctgtttgcaa agtgatgact tgccatacac gttcggaggg   300
gggaccaagc tggaaataaa acgg                                          324
```

<210> SEQ ID NO 7
<211> LENGTH: 108
<212> TYPE: PRT
<213> ORGANISM: Mus musculus

<400> SEQUENCE: 7

```
Glu Thr Thr Val Thr Gln Ser Pro Ala Ser Leu Ser Met Ala Ile Gly
1               5                   10                  15

Gly Lys Val Thr Ile Arg Cys Ile Ile Ser Thr Asn Ile Asp Asp Asp
            20                  25                  30

Ile Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asp Leu Pro Tyr
                85                  90                  95

Thr Phe Gly Gly Gly Thr Lys Leu Glu Ile Lys Arg
            100                 105
```

<210> SEQ ID NO 8
<211> LENGTH: 351
<212> TYPE: DNA
<213> ORGANISM: Mus musculus

<400> SEQUENCE: 8

```
gaggtccagc tgcaacagtc tggacctgag ctggtaaagc ctggagcttc aatgaagata    60
tcctgcaagg cttctggtta ctcattcact ggctacccca tgaactgggt gaggcagagc   120
catggaaaga accttgagtg gattggactt attaatcctt acaatggtga ctactttc     180 aaccagaaat tcaagggcaa ggccacatta actgtagaca gtcatccag cacagcctac    240 atggaactcc tcagtctgac ttctgaggac tctgcagtct attactgtgc aagagggacg   300
tatgaatatg ttgactactg gggccaaggc accactctca cagtctcctc a            351
```

<210> SEQ ID NO 9
<211> LENGTH: 117
<212> TYPE: PRT
<213> ORGANISM: Mus musculus

<400> SEQUENCE: 9

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Pro Met Asn Trp Val Arg Gln Ser His Gly Lys Asn Leu Glu Trp Ile
        35                  40                  45

Gly Leu Ile Asn Pro Tyr Asn Gly Asp Thr Thr Phe Asn Gln Lys Phe
```

```
Lys Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Gly Thr Tyr Glu Tyr Val Asp Tyr Trp Gly Gln Gly Thr Thr
            100                 105                 110

Leu Thr Val Ser Ser
        115

<210> SEQ ID NO 10
<211> LENGTH: 321
<212> TYPE: DNA
<213> ORGANISM: Mus musculus

<400> SEQUENCE: 10
caaattgttc tcacccagtc tccaacaatc atgtctgcat ctccagggga gagagtcacc      60
atgacctgca gtgccagctc aagtgtattt tacatgcact ggtaccagca gaagccaggg     120
tcctccccca gactcctgat ttatgacaca tccatcctgt cttctggagt ccctgttcgc     180
ttcagtggca gtgggtctgg gacctcttac tctctcacaa tcagacgaat ggaggctgaa     240
gatgctgcca cttattactg ccagcagtgg agtagttacc ctctcacgtt cggtgctggg     300
accaagctgg agctgaaacg g                                               321

<210> SEQ ID NO 11
<211> LENGTH: 107
<212> TYPE: PRT
<213> ORGANISM: Mus musculus

<400> SEQUENCE: 11

Gln Ile Val Leu Thr Gln Ser Pro Thr Ile Met Ser Ala Ser Pro Gly
 1               5                  10                  15

Glu Arg Val Thr Met Thr Cys Ser Ala Ser Ser Ser Val Phe Tyr Met
                 20                  25                  30

His Trp Tyr Gln Gln Lys Pro Gly Ser Ser Pro Arg Leu Leu Ile Tyr
            35                  40                  45

Asp Thr Ser Ile Leu Ser Ser Gly Val Pro Val Arg Phe Ser Gly Ser
    50                  55                  60

Gly Ser Gly Thr Ser Tyr Ser Leu Thr Ile Arg Arg Met Glu Ala Glu
 65                  70                  75                  80

Asp Ala Ala Thr Tyr Tyr Cys Gln Gln Trp Ser Ser Tyr Pro Leu Thr
                 85                  90                  95

Phe Gly Ala Gly Thr Lys Leu Glu Leu Lys Arg
            100                 105

<210> SEQ ID NO 12
<211> LENGTH: 366
<212> TYPE: DNA
<213> ORGANISM: Mus musculus

<400> SEQUENCE: 12
gaggttcagc tccagcagtc tgggactgtg ctggcaaggc ctggggcttc cgtgaagatg      60
tcctgcaagg cttctggcta cagctttacc acctactgga tacactgggt taagcagagg     120
cctggacagg gtctagaatg gattggtgct attgatcctg aaatagtga tgctacctac      180 agccagaagt tcaaggacaa ggccaaactg actgcagtca catccgccag cactgccttc     240
```

```
atggagctca acagcctgac aaatgatgac tctgcggtct attactgttc aagagaagtc    300
tactatggtt acgacgggga ctactttgac tactggggcc aaggcaccac tctcacagtc    360
tcctca                                                                366
```

<210> SEQ ID NO 13
<211> LENGTH: 122
<212> TYPE: PRT
<213> ORGANISM: Mus musculus

<400> SEQUENCE: 13

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Thr Tyr
            20                  25                  30

Trp Ile His Trp Val Lys Gln Arg Pro Gly Gln Gly Leu Glu Trp Ile
        35                  40                  45

Gly Ala Ile Asp Pro Gly Asn Ser Asp Ala Thr Tyr Ser Gln Lys Phe
    50                  55                  60

Lys Asp Lys Ala Lys Leu Thr Ala Val Thr Ser Ala Ser Thr Ala Phe
65                  70                  75                  80

Met Glu Leu Asn Ser Leu Thr Asn Asp Asp Ser Ala Val Tyr Tyr Cys
                85                  90                  95

Ser Arg Glu Val Tyr Tyr Gly Tyr Asp Gly Asp Tyr Phe Asp Tyr Trp
            100                 105                 110

Gly Gln Gly Thr Thr Leu Thr Val Ser Ser
        115                 120
```

<210> SEQ ID NO 14
<211> LENGTH: 336
<212> TYPE: DNA
<213> ORGANISM: Mus musculus

<400> SEQUENCE: 14

```
gacattgtgc tgacccaatc tccagcttct ttggctgtgt ctctagggca gagggccacc     60
atctcctgca gagccagtga aagtgtcagt gttcatggta ctcatttaat gcactggtac    120
caacagaaac aggacagcc acccaaactc ctcatctatg ctgcatccaa gctagaatct     180
ggagtccctg ccaggttcag tggcagtggg tctgagacag acttcaccct caacatccat    240
cctgtggagg aggaggatgc tgcaacctat ttctgtcagc aaagtattgg ggatccgtgg    300
acgttcggtg gaggcaccaa gctggaaatc aaacgg                              336
```

<210> SEQ ID NO 15
<211> LENGTH: 112
<212> TYPE: PRT
<213> ORGANISM: Mus musculus

<400> SEQUENCE: 15

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Val His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Lys Leu Glu Ser Gly Val Pro Ala
    50                  55                  60

Arg Phe Ser Gly Ser Gly Ser Glu Thr Asp Phe Thr Leu Asn Ile His
```

```
                     65                  70                  75                  80
Pro Val Glu Glu Glu Asp Ala Ala Thr Tyr Phe Cys Gln Gln Ser Ile
                85                  90                  95
Gly Asp Pro Trp Thr Phe Gly Gly Gly Thr Lys Leu Glu Ile Lys Arg
            100                 105                 110
```

<210> SEQ ID NO 16
<211> LENGTH: 32
<212> TYPE: DNA
<213> ORGANISM: Artificial sequence
<220> FEATURE:
<223> OTHER INFORMATION: Reverse primer

<400> SEQUENCE: 16
cttgccattg agccagtcct ggtgcatgat gg                                  32

<210> SEQ ID NO 17
<211> LENGTH: 23
<212> TYPE: DNA
<213> ORGANISM: Artificial sequence
<220> FEATURE:
<223> OTHER INFORMATION: Reverse primer

<400> SEQUENCE: 17
gttgttcaag aagcacacga ctg                                            23

<210> SEQ ID NO 18
<211> LENGTH: 36
<212> TYPE: DNA
<213> ORGANISM: Artificial sequence
<220> FEATURE:
<223> OTHER INFORMATION: Reverse primer

<400> SEQUENCE: 18
gctctagact aacactcatt cctgttgaag ctcttg                              36

<210> SEQ ID NO 19
<211> LENGTH: 406
<212> TYPE: PRT
<213> ORGANISM: Homo sapiens

<400> SEQUENCE: 19

```
Ala Asn Ala Phe Leu Glu Glu Leu Arg Pro Gly Ser Leu Glu Arg Glu
1               5                   10                  15
Cys Lys Glu Glu Gln Cys Ser Phe Glu Glu Ala Arg Glu Ile Phe Lys
                20                  25                  30
Asp Ala Glu Arg Thr Lys Leu Phe Trp Ile Ser Tyr Ser Asp Gly Asp
            35                  40                  45
Gln Cys Ala Ser Ser Pro Cys Gln Asn Gly Gly Ser Cys Lys Asp Gln
        50                  55                  60
Leu Gln Ser Tyr Ile Cys Phe Cys Leu Pro Ala Phe Glu Gly Arg Asn
65                  70                  75                  80
Cys Glu Thr His Lys Asp Asp Gln Leu Ile Cys Val Asn Glu Asn Gly
                85                  90                  95
Gly Cys Glu Gln Tyr Cys Ser Asp His Thr Gly Thr Lys Arg Ser Cys
            100                 105                 110
Arg Cys His Glu Gly Tyr Ser Leu Leu Ala Asp Gly Val Ser Cys Thr
        115                 120                 125
Pro Thr Val Glu Tyr Pro Cys Gly Lys Ile Pro Ile Leu Glu Lys Arg
    130                 135                 140
```

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 20
<211> LENGTH: 2332
<212> TYPE: PRT
<213> ORGANISM: Homo sapiens

<400> SEQUENCE: 20

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

```
Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
        130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
        370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525
```

-continued

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp

-continued

```
            945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
                980                 985                 990
Val Ser Ile Ser Leu Leu Lys Thr Asn Lys Thr Ser Asn Asn Ser Ala
                995                1000                1005
Thr Asn Arg Lys Thr His Ile Asp Gly Pro Ser Leu Leu Ile Glu
       1010                1015                1020
Asn Ser Pro Ser Val Trp Gln Asn Ile Leu Glu Ser Asp Thr Glu
       1025                1030                1035
Phe Lys Lys Val Thr Pro Leu Ile His Asp Arg Met Leu Met Asp
       1040                1045                1050
Lys Asn Ala Thr Ala Leu Arg Leu Asn His Met Ser Asn Lys Thr
       1055                1060                1065
Thr Ser Ser Lys Asn Met Glu Met Val Gln Gln Lys Lys Glu Gly
       1070                1075                1080
Pro Ile Pro Pro Asp Ala Gln Asn Pro Asp Met Ser Phe Phe Lys
       1085                1090                1095
Met Leu Phe Leu Pro Glu Ser Ala Arg Trp Ile Gln Arg Thr His
       1100                1105                1110
Gly Lys Asn Ser Leu Asn Ser Gly Gln Gly Pro Ser Pro Lys Gln
       1115                1120                1125
Leu Val Ser Leu Gly Pro Glu Lys Ser Val Glu Gly Gln Asn Phe
       1130                1135                1140
Leu Ser Glu Lys Asn Lys Val Val Val Gly Lys Gly Glu Phe Thr
       1145                1150                1155
Lys Asp Val Gly Leu Lys Glu Met Val Phe Pro Ser Ser Arg Asn
       1160                1165                1170
Leu Phe Leu Thr Asn Leu Asp Asn Leu His Glu Asn Asn Thr His
       1175                1180                1185
Asn Gln Glu Lys Lys Ile Gln Glu Glu Ile Glu Lys Lys Glu Thr
       1190                1195                1200
Leu Ile Gln Glu Asn Val Val Leu Pro Gln Ile His Thr Val Thr
       1205                1210                1215
Gly Thr Lys Asn Phe Met Lys Asn Leu Phe Leu Leu Ser Thr Arg
       1220                1225                1230
Gln Asn Val Glu Gly Ser Tyr Asp Gly Ala Tyr Ala Pro Val Leu
       1235                1240                1245
Gln Asp Phe Arg Ser Leu Asn Asp Ser Thr Asn Arg Thr Lys Lys
       1250                1255                1260
His Thr Ala His Phe Ser Lys Lys Gly Glu Glu Glu Asn Leu Glu
       1265                1270                1275
Gly Leu Gly Asn Gln Thr Lys Gln Ile Val Glu Lys Tyr Ala Cys
       1280                1285                1290
Thr Thr Arg Ile Ser Pro Asn Thr Ser Gln Gln Asn Phe Val Thr
       1295                1300                1305
Gln Arg Ser Lys Arg Ala Leu Lys Gln Phe Arg Leu Pro Leu Glu
       1310                1315                1320
Glu Thr Glu Leu Glu Lys Arg Ile Ile Val Asp Asp Thr Ser Thr
       1325                1330                1335
Gln Trp Ser Lys Asn Met Lys His Leu Thr Pro Ser Thr Leu Thr
       1340                1345                1350
```

```
Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740
```

```
Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
```

```
            2135                2140                2145

Ile Arg Leu His Pro Thr His Tyr Ser Ile Arg Ser  Thr Leu Arg
        2150                2155                2160

Met Glu Leu Met Gly Cys Asp Leu Asn Ser Cys Ser  Met Pro Leu
    2165                2170                2175

Gly Met Glu Ser Lys Ala Ile Ser Asp Ala Gln Ile  Thr Ala Ser
        2180                2185                2190

Ser Tyr Phe Thr Asn Met Phe Ala Thr Trp Ser Pro  Ser Lys Ala
    2195                2200                2205

Arg Leu His Leu Gln Gly Arg Ser Asn Ala Trp Arg  Pro Gln Val
        2210                2215                2220

Asn Asn Pro Lys Glu Trp Leu Gln Val Asp Phe Gln  Lys Thr Met
    2225                2230                2235

Lys Val Thr Gly Val Thr Thr Gln Gly Val Lys Ser  Leu Leu Thr
        2240                2245                2250

Ser Met Tyr Val Lys Glu Phe Leu Ile Ser Ser Ser  Gln Asp Gly
    2255                2260                2265

His Gln Trp Thr Leu Phe Phe Gln Asn Gly Lys Val  Lys Val Phe
        2270                2275                2280

Gln Gly Asn Gln Asp Ser Phe Thr Pro Val Val Asn  Ser Leu Asp
    2285                2290                2295

Pro Pro Leu Leu Thr Arg Tyr Leu Arg Ile His Pro  Gln Ser Trp
        2300                2305                2310

Val His Gln Ile Ala Leu Arg Met Glu Val Leu Gly  Cys Glu Ala
    2315                2320                2325

Gln Asp Leu Tyr
    2330

<210> SEQ ID NO 21
<211> LENGTH: 414
<212> TYPE: PRT
<213> ORGANISM: Homo sapiens

<400> SEQUENCE: 21

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Pro Ala Val Pro
        115                 120                 125

Phe Pro Cys Gly Arg Val Ser Val Ser Gln Thr Ser Lys Leu Thr Arg
    130                 135                 140

Ala Glu Ala Val Phe Pro Asp Val Asp Tyr Val Asn Ser Thr Glu Ala
145                 150                 155                 160
```

Glu Thr Ile Leu Asp Asn Ile Thr Gln Ser Thr Gln Ser Phe Asn Asp
            165                 170                 175

Phe Thr Arg Val Val Gly Gly Glu Asp Ala Lys Pro Gly Gln Phe Pro
        180                 185                 190

Trp Gln Val Val Leu Asn Gly Lys Val Asp Ala Phe Cys Gly Gly Ser
    195                 200                 205

Ile Val Asn Glu Lys Trp Ile Val Thr Ala Ala His Cys Val Glu Thr
210                 215                 220

Gly Val Lys Ile Thr Val Val Ala Gly Glu His Asn Ile Glu Glu Thr
225                 230                 235                 240

Glu His Thr Glu Gln Lys Arg Asn Val Ile Arg Ile Ile Pro His His
            245                 250                 255

Asn Tyr Asn Ala Ala Ile Asn Lys Tyr Asn His Asp Ile Ala Leu Leu
        260                 265                 270

Glu Leu Asp Glu Pro Leu Val Leu Asn Ser Tyr Val Thr Pro Ile Cys
    275                 280                 285

Ile Ala Asp Lys Glu Tyr Thr Asn Ile Phe Leu Lys Phe Gly Ser Gly
290                 295                 300

Tyr Val Ser Gly Trp Gly Arg Val Phe His Lys Gly Arg Ser Ala Leu
305                 310                 315                 320

Val Leu Gln Tyr Leu Arg Val Pro Leu Val Asp Arg Ala Thr Cys Leu
            325                 330                 335

Arg Ser Thr Lys Phe Thr Ile Tyr Asn Asn Met Phe Cys Ala Gly Phe
        340                 345                 350

His Glu Gly Gly Arg Asp Ser Cys Gln Gly Asp Ser Gly Gly Pro His
    355                 360                 365

Val Thr Glu Val Glu Gly Thr Ser Phe Leu Thr Gly Ile Ile Ser Trp
370                 375                 380

Gly Glu Glu Cys Ala Met Lys Gly Lys Tyr Gly Ile Tyr Thr Lys Val
385                 390                 395                 400

Ser Arg Tyr Val Asn Trp Ile Lys Glu Lys Thr Lys Leu Thr
            405                 410

<210> SEQ ID NO 22
<211> LENGTH: 240
<212> TYPE: PRT
<213> ORGANISM: Homo sapiens

<400> SEQUENCE: 22

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

```
Gly Cys Leu Gly Asn Met Asn Asn Phe Glu Thr Leu Glu Glu Cys Lys
            130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
                180                 185                 190

Ala Asp Arg Gly Leu Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
            210                 215                 220

Asn Glu Asn Asn Phe Thr Ser Lys Gln Glu Cys Leu Arg Ala Cys Lys
225                 230                 235                 240

<210> SEQ ID NO 23
<211> LENGTH: 241
<212> TYPE: PRT
<213> ORGANISM: Homo sapiens

<400> SEQUENCE: 23

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
            130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
                180                 185                 190

Ala Asp Arg Gly Leu Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
            210                 215                 220

Asn Glu Asn Asn Phe Thr Ser Lys Gln Glu Cys Leu Arg Ala Cys Lys
225                 230                 235                 240

Lys

<210> SEQ ID NO 24
```

<211> LENGTH: 242
<212> TYPE: PRT
<213> ORGANISM: Homo sapiens

<400> SEQUENCE: 24

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly

<210> SEQ ID NO 25
<211> LENGTH: 243
<212> TYPE: PRT
<213> ORGANISM: Homo sapiens

<400> SEQUENCE: 25

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

```
Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
            130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
            210                 215                 220

Asn Glu Asn Asn Phe Thr Ser Lys Gln Glu Cys Leu Arg Ala Cys Lys
225                 230                 235                 240

Lys Gly Phe

<210> SEQ ID NO 26
<211> LENGTH: 244
<212> TYPE: PRT
<213> ORGANISM: Homo sapiens

<400> SEQUENCE: 26

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
            85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
            130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190
```

```
Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile
```